(12) United States Patent
Welch et al.

(10) Patent No.: US 9,577,037 B2
(45) Date of Patent: Feb. 21, 2017

(54) NANOCRYSTALS WITH HIGH EXTINCTION COEFFICIENTS AND METHODS OF MAKING AND USING SUCH NANOCRYSTALS

(75) Inventors: Eric Welch, Eugene, OR (US); Joseph Bartel, Carlsbad, CA (US); Eric Tulsky, Berkeley, CA (US); Joseph Treadway, Eugene, OR (US); Yongfen Chen, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 140 days.

(21) Appl. No.: 13/997,598

(22) PCT Filed: Dec. 23, 2011

(86) PCT No.: PCT/US2011/067174
§ 371 (c)(1),
(2), (4) Date: Sep. 16, 2013

(87) PCT Pub. No.: WO2012/092195
PCT Pub. Date: Jul. 5, 2012

(65) Prior Publication Data
US 2014/0001436 A1    Jan. 2, 2014

Related U.S. Application Data

(60) Provisional application No. 61/427,760, filed on Dec. 28, 2010, provisional application No. 61/441,579, filed on Feb. 10, 2011.

(51) Int. Cl.
*C09K 11/08* (2006.01)
*B82Y 30/00* (2011.01)
(Continued)

(52) U.S. Cl.
CPC .......... *H01L 29/0665* (2013.01); *B82Y 30/00* (2013.01); *C30B 7/00* (2013.01); *C30B 29/40* (2013.01);
(Continued)

(58) Field of Classification Search
CPC ............ G06K 19/06084; G01N 33/582; G01N 33/587; G01N 33/588; G01N 33/533; H01L 51/0007; H01L 31/055; H01L 31/0296; H01L 31/022483; H01L 31/035218; H01L 29/0665; H01L 21/02628; A61K 49/0065; A61K 49/0067; A61K 49/0093; G02F 1/133614; B82Y 15/00; B82Y 30/00; B82Y 20/00; B82Y 40/00; C30B 7/00
(Continued)

(56) References Cited

U.S. PATENT DOCUMENTS 5,262,357 A    11/1993    Alivisatos et al.
5,505,928 A     4/1996    Alivisatos et al.
(Continued)

FOREIGN PATENT DOCUMENTS

WO    WO99/26299       5/1999
WO    WO-2009/025913   2/2009
(Continued)

OTHER PUBLICATIONS

Aharoni, A. et al., "Synthesis of InAs/CdSe/ZnSe Core/Shell1/Shell2 Structures with Bright and Stable Near-Infrared Fluorescence", *J. Am. Chem. Soc.*, vol. 128 (1), 2006, 257-264.
(Continued)

*Primary Examiner* — Matthew Landau
*Assistant Examiner* — Stephen C Smith

(57) ABSTRACT

A population of bright and stable nanocrystals is provided. The nanocrystals include a semiconductor core and a thick
(Continued)

semiconductor shell and can exhibit high extinction coefficients, high quantum yields, and limited or no detectable blinking.

20 Claims, 2 Drawing Sheets

(51) Int. Cl.

| | | |
|---|---|---|
| H01L 29/06 | (2006.01) | |
| C30B 7/00 | (2006.01) | |
| C30B 29/40 | (2006.01) | |
| C30B 29/48 | (2006.01) | |
| C30B 29/60 | (2006.01) | |
| G01N 33/533 | (2006.01) | |
| H01L 51/00 | (2006.01) | |
| H01L 21/02 | (2006.01) | |
| C09K 11/56 | (2006.01) | |
| C09K 11/57 | (2006.01) | |
| C09K 11/02 | (2006.01) | |
| B82Y 15/00 | (2011.01) | |
| G01N 33/58 | (2006.01) | |
| B82Y 40/00 | (2011.01) | |
| B82Y 20/00 | (2011.01) | |

(52) U.S. Cl.
CPC ............... *C30B 29/48* (2013.01); *C30B 29/60* (2013.01); *G01N 33/533* (2013.01); *H01L 21/02628* (2013.01); *H01L 51/0007* (2013.01); *B82Y 20/00* (2013.01); *B82Y 40/00* (2013.01)

(58) Field of Classification Search
USPC .......................................................... 257/13
See application file for complete search history.

(56) References Cited

U.S. PATENT DOCUMENTS

| | | |
|---|---|---|
| 5,690,807 A | 11/1997 | Clark, Jr. et al. |
| 5,990,479 A | 11/1999 | Weiss et al. |
| 6,048,616 A | 4/2000 | Gallagher et al. |
| 6,207,229 B1 | 3/2001 | Bawendi et al. |
| 6,207,299 B1 | 3/2001 | Krauth |
| 6,322,901 B1 | 11/2001 | Bawendi et al. |
| 6,576,291 B2 | 6/2003 | Bawendi et al. |
| 6,649,138 B2 | 11/2003 | Adams et al. |
| 6,727,065 B2 | 4/2004 | Weiss et al. |
| 6,815,064 B2 * | 11/2004 | Treadway et al. ............ 428/403 |
| 7,253,452 B2 | 8/2007 | Steckel et al. |
| 7,288,468 B2 | 10/2007 | Jang |
| 7,615,800 B2 | 11/2009 | Kahen |
| 7,767,260 B2 | 8/2010 | Peng et al. |
| 7,935,419 B1 | 5/2011 | Hollingsworth et al. |
| 8,404,154 B2 * | 3/2013 | Breen et al. ........... 252/301.6 S |
| 8,637,082 B2 | 1/2014 | Tulsky et al. |
| 2003/0136943 A1 | 7/2003 | Alivisatos |
| 2006/0057382 A1 * | 3/2006 | Treadway et al. ............ 428/403 |
| 2006/0157720 A1 | 7/2006 | Bawendi et al. |
| 2007/0289491 A1 | 12/2007 | Peng et al. |
| 2008/0220593 A1 | 9/2008 | Pickett et al. |
| 2008/0280223 A1 | 11/2008 | Levy et al. |
| 2010/0163800 A1 | 7/2010 | Peng et al. |
| 2010/0308271 A1 | 12/2010 | Bartel |
| 2012/0157824 A1 * | 6/2012 | Bossmann ....... G01N 33/54346 600/420 |

FOREIGN PATENT DOCUMENTS

| | | | |
|---|---|---|---|
| WO | WO2009/136974 | 11/2009 | |
| WO | WO 2010/002540 | * 1/2010 | ............ G01N 33/50 |
| WO | WO-2010/002540 | 1/2010 | |
| WO | WO2010/039897 | 4/2010 | |
| WO | WO2010/040074 | 4/2010 | |
| WO | WO2010/040109 | 4/2010 | |
| WO | WO2010/040111 | 4/2010 | |
| WO | WO2010/048580 | 4/2010 | |
| WO | WO2010/048581 | 4/2010 | |
| WO | WO2010/096084 | 8/2010 | |
| WO | WO2012/027203 A1 | 3/2012 | |
| WO | WO2012/092178 A1 | 7/2012 | |

OTHER PUBLICATIONS

Dabbousi, B. O. et al., "(Cdse)Zns Core-Shell Quantum Dots: Synthesis and Characterizations of a Size Series of Highly Luminescent Nanocrystallites", *J. Phys. Chem. B*, vol. 101, No. 46, Jun. 26, 1997, 9463-9475.

PCT/US2011/067174, , "European Search Report Mailed Nov. 13, 2014", Nov. 13, 2014, 9 Pages.

Alivisatos, A., "Semiconductor Clusters, Nanocrystals, and Quantum Dots", 271, 1996, 933-937.

Bruchez, Marcel P. et al., "Luminescent Semiconductor Nanocrystals: Intermitten Behaviour and Use as Fluorescent Biological Probes", *UMI Dissertation Information Service*, 1998, 1-115.

Chen, Yongfen et al., ""Giant" Multishell CdSe Nanocrystal Quantum Dots with Suppressed Blinking", *J. Am. Chem. Soc.*, 130 (15), 2008, 5026-5027.

Coffer, Jeffery L. et al., "Characterization of quantum-confined CdS nanocrystallites stabilized by deoxyribonucleic acid (DNA)", *Nanotechnology*, vol. 3, 1992, 69-76.

Danek, M. et al., "Preparation of II-VI quantum dot composites by electrospray organometallic chemical vapor deposition", *J. Cryst. Growth*, 145, Issues 1-4, 1994, 714-720.

Efros, A. et al., "Band-edge exciton in quantum dots of semiconductors with a degenerate valence band: dark and bright exciton 4856 states", *Physical Review B.* vol. 54, Issue 7, 1996, 4843-4856.

Evans, Christopher et al., "Mysteries of TOPSe Revealed: Insights into Quantum Dot Nucleation", *J. Am. Chem. Soc.*, 132, 2010, 10973-10975.

Forster, T., "Intermolecular energy migration and fluorescence", *Annalen der Physik*, vol. 437(1-2), 1948, 55-75.

Galland, Christophe et al., "Two Types of Luminscenece Blinking Revealed by Spectroelectrochemistry of Single Quantum Dots", *Nature*, vol. 479, Nov. 2011, 203-208.

García-Santamaría, Florencio et al., "Suppressed Auger Recombination in "Giant" Nanocrystals Boosts Optical Gain Performance", *Nano Lett.*, 9 (10), 2009, 3482-3488.

Grabolle, M et al., "Stability and Fluorescence Quantum Yield of CdSe—ZnS Quatum Dots-Influence of the Thickness of the ZnS Shell", *Ann. N. Y. Acad. Sci*, 1130, 2008, 235-241.

Greytak, A. et al., "Alternating layer addition approach to CdSe/CdS core/shell quantum dots with near-unity quantum yield and high on-time fractions", *Chem. Sci.*, vol. 3, 2012, pp. 2028-2034.

Hines, Margaret A. et al., "Synthesis and Characterization of Strongly Luminescing ZnS-Capped CdSe Nanocrystals", *J. Phys. Chem.*, vol. 100, No. 2, 1996, 468-471.

Ivanov, et al., "Typed-II Core/Shell CdS/ZnSe Nanocrystals: Synthesis, Electronic Structures, and Spectroscopic Properties", *J. Am. Chem. Soc.*, 2005, 11708-11719.

Kortan, A. R. et al., "Nucleation and growth of Cdse on ZnS Quantum crystallite seeds, and vice versa, in inverse Micelle Media.", *J. Am. Chem. Soc.*, vol. 112, 1990, 1327-1332.

Kuno, M: et al., The Band Edge Luminescence of Surface Modified CDSE Nanocrystallites Probing the Luminescence State >>, *Journal of Chemical Physics*, American Institute of Physics, New York, NY, vol. 1. 106, No. 23, 1997, 9869-9882.

Lakowicz, J.R., "Energy Transfer", *Principles of Fluorescence Spectroscopy, 2nd Ed. Plenum Publishing Corp.*, New York, NY, 1999, 367-394.

Mahler, B. et al., "Towards non-blinking colloidal quantum dots", *Nature Materials*, vol. 7, 2008, pp. 659-664.

McBride, J. et al., "Structural Basis for Near Unity Quantum Yield Core/Shell Nanostructures", *Nano Letters*, vol. 6, No. 7, 2006, 1496-1501.

(56) References Cited

OTHER PUBLICATIONS

Murray, C. B. et al., "Synthesis and Characterization of Nearly Monodisperse CdE (E=S, Se, Te) Semiconductor Nanocrystallites", *J. Am. Chem. Soc.*, vol. 115, No. 19, 1993, 8706-8715.

Nirmal, Manoj et al., "Luminescence Photophysics in Semiconductor Nanocrystals", *Acc. Chem. Res.*, 32 (5), 1999, 407-414.

PCT/US11/67144, "International Search Report", Mailed Apr. 27, 2012.

PCT/US11/67144, "Written Opinion", Mailed Apr. 27, 2012, pp. 1-11.

Peng, et al., "Epitaxial growth of highly luminescent Cdse/cdS core/Shell Nanocrystals with photostability and electronic accessibility", *J. Am. Soc.*, vol. 119, 1997, 7019-7029.

Premachandran, et al., ""The Enzymatic Synthesis of Thiol-Containing Polymers to prepare Polymer-Cds Nanocomposites"", *Chem. Mater.* 9(6), 1997, 1342-1347.

Qu, Lianhua et al., "Alternative Routes Toward High Quality CdSe Nanocrystals", *Nano Letters*, vol. 1, No. 6, 2001, 333-337.

Reiss, Peter et al., "Core/Shell Semiconductor Nanocrystals", vol. 5 (2), 2009, 154-158.

Wang, Fudong et al., "Spectroscopic Identification of Tri-n-octylphosphine Oxide (TOPO) Impurities and Elucidation of Their Roles in Cadmium Selenide Quantum-Wire Growth", *Department of Chemistry*, Washington University, Jan. 14, 2009, 1-38.

Wang, Fudong et al., "The Trouble with TOPO; Identification of Adventitious Impurities Beneficial to the Growth of Cadmium Selenide Quantum Dots, Rods, and Wires", *Nano. Lett.*, 8(10), 2008, 3521-3524.

Xie, R. et al., "Synthesis and Characterization of Highly Luminescent CdSe-Core CdS/Zn0.5Cd0.5S/ZnS Multishell Nancrystals.", *J. Am. Chem. Soc..* 127, 2005, 7480-7488.

Yu, W. William et al., "Experimental Determination of the Extinction Coefficient of CdTe, CdSe, and CdS Nanocrystals", *Chem. Mater.*, 15 (14), 2003, 2854-2860.

Zhong, Xinhua et al., "Composition-Turntable, ZnxCd1—xSe Nanocrystals with High Luminescence and stability", *Journal of the American Chemical Society*, vol. 125, No. 28, Jun. 21, 2003, 8589-8594.

Molecular Probes, "Product sheet for Qdot® 625 Streptavidin Conjugates", 2007, pp. 1-15.

\* cited by examiner

NANOCRYSTALS WITH HIGH EXTINCTION COEFFICIENTS AND METHODS OF MAKING AND USING SUCH NANOCRYSTALS

CROSS-REFERENCE TO RELATED APPLICATIONS

This application is a 371 of International Application No. PCT/US2011/067174, filed Dec. 23, 2011, which claims the benefit under 35 U.S.C. §119(e) of U.S. Provisional Application Ser. No. 61/427,760, filed Dec. 28, 2010, and U.S. Provisional Application Ser. No. 61/441,579, filed Feb. 10, 2011, the disclosures of which are hereby incorporated by reference as if set forth in full.

TECHNICAL FIELD

This application relates to nanocrystals having high extinction coefficients that are useful in a variety of fields including biology, analytical and combinatorial chemistry, medical diagnostics, genetic analysis, solar energy conversion, displays, anti-counterfeiting, and single molecule spectroscopy; and methods for their preparation and use.

BACKGROUND

Semiconductor nanocrystals with small diameters can have properties intermediate between molecular and bulk forms of matter. Small diameter semiconductor materials can exhibit quantum confinement of both the electron and hole in three dimensions. Quantum confinement plays a key role in determining the size-dependent optical properties of semiconductor nanocrystals. One effect of quantum confinement is an increase in the effective band gap of the material with decreasing nanocrystal size. As the size of the semiconductor nanocrystal decreases, both the optical absorption and emission of the nanocrystals shift to higher energy (i.e., to the blue). The extinction coefficient is also size-dependent. As the size of a nanocrystal increases, the extinction coefficient of the particle increases proportionally. Consequently, for a given material, larger semiconductor nanocrystals (e.g., nanocrystals emitting in the red or IR spectral region) are typically brighter than smaller nanocrystals (e.g., nanocrystals emitting at wavelengths below the red spectral region).

Nanocrystals frequently include a semiconductor core and a passivating, semiconductor shell. Shell materials with bandgaps higher than those of the core materials can minimize deep-trap emission sites and can enhance quantum yield (QY) and stability of the nanocrystal particle. The optical properties (e.g., brightness) and stability of the nanocrystal can be further improved by the use of very thick shells. However, a common drawback of using thick shells to enhance the brightness of nanocrystals is an associated shift of the emission band to longer wavelengths (i.e., red-shifting). This can be a problem for applications where both bright materials and multiple colors spanning the visible spectrum (e.g., blue to red) are required. Further, currently available nanocrystals, especially those with lower emission wavelengths, are often insufficiently bright, typically exhibit pronounced levels of intermittent blinking and are not often photostable under prolonged irradiation.

Thus, there is a need to develop approaches to provide bright and stable nanocrystals having high QY and/or high extinction coefficients. A need also exists for bright and stable semiconductor nanocrystals with high energy emission in the visible or UV regions of the electromagnetic spectrum (e.g., blue, green, yellow, and orange). A further need exists to provide small (such that they are useful in fluorescence resonance energy transfer or cell nucleus staining applications) and stable nanocrystals which address the problems posed by nanocrystal fluorescent intermittency (as this intermittency complicates the reliable use of "blinking" nanocrystals as a single photon light source for quantum informatics and as biolabels for real-time monitoring of single biomolecules).

SUMMARY

Provided herein are nanocrystals that exhibit narrow fluorescence emission bands over the UV, visible and IR spectral regions, kits and compositions including such nanocrystals, as well as methods of producing and using such nanocrystals. The described nanocrystals can be exceptionally bright, exhibit modulated, reduced or no intermittent (e.g., continuous, non-blinking) fluorescence, and chemically and photochemically stable. Thus, the described nanocrystals overcome many of the disadvantages associated with conventional fluorescent semiconductor nanocrystals. Due to their exceptional optical properties, these nanocrystals can function as powerful detection tools in a variety of life science applications ranging from cell and tissue staining (e.g., FISH), cell tracking, Western blot detection of proteins, visualization of cell migration, single-molecule detection, flow cytometric analysis to in vivo imaging. Additionally, these nanocrystals can form foundational components in LEDs, solar cells, transistors, and diode lasers and have numerous non-biological applications, such as anti-counterfeiting.

The nanocrystals described herein typically include at least one semiconductor material. Thus, in one aspect, a population of nanocrystals is provided, wherein each nanocrystal in the population includes a) a semiconductor core; and b) a semiconductor shell disposed on the semiconductor core, wherein each nanocrystal in the population has a nanocrystal volume to core volume ratio ($V_{core+shell}/V_{core}$) of 10:1 or greater.

In yet another aspect, a population of nanocrystals is provided, wherein each nanocrystal in the population includes a) a semiconductor core; and b) a semiconductor shell disposed on the semiconductor core, wherein the nanocrystal volume to core volume ratio ($V_{core+shell}/V_{core}$) of each nanocrystal is greater than about 5:1, wherein the population has a maximum fluorescence emission wavelength less than about 620 nm.

In another aspect, a population of nanocrystals is provided, wherein each nanocrystal in the population includes a) a semiconductor core; and b) a semiconductor shell disposed on the semiconductor core, wherein the ratio of the absorbance intensity of the population measured at an excitation wavelength of 405 nm to the absorbance intensity measured at the band edge absorbance wavelength ($A_{405\,nm}/A_{band-edge}$) is 20 or greater.

In yet another aspect, a population of nanocrystals is provided, wherein the ratio of the absorbance intensity of the population measured at an excitation wavelength of 405 nm to the absorbance intensity measured at the band edge absorbance wavelength ($A_{405\,nm}/A_{band-edge}$) is about 10 or greater; wherein the population has a maximum fluorescence emission wavelength less than about 620 nm. In certain embodiments, $A_{405\,nm}/A_{band-edge}$ is about 15 or greater; or about 25 or greater; or about 15 to about 50.

In yet another aspect, a population of nanocrystals is provided, wherein each nanocrystal in the population includes a) a semiconductor core; and b) a semiconductor shell disposed on the semiconductor core, wherein the ratio of absorbance intensity of the population measured at an excitation wavelength of 405 nm to the absorbance intensity of the population measured at an excitation wavelength that is 25 nm less than the band edge emission wavelength ($A_{405\ nm}/A_{(\lambda em-25\ nm)}$) is about 20 or greater.

In yet another aspect, a population of nanocrystals is provided, wherein the ratio of absorbance intensity of the population measured at an excitation wavelength of 405 nm to the absorbance intensity of the population measured at an excitation wavelength that is 25 nm less than the band edge emission wavelength ($A_{405\ nm}/A_{(\lambda em-25\ nm)}$) is 10 or greater, wherein the population has a maximum fluorescence emission wavelength less than about 620 nm. In certain embodiments, $A_{405\ nm}/A_{(\lambda em-25\ nm)}$ is 15 or greater; or 25 or greater; or about 15 to about 50.

In yet another aspect, a population of nanocrystals is provided, wherein each nanocrystal in the population includes a) a semiconductor core; and b) a semiconductor shell disposed on the semiconductor core, wherein the extinction coefficient of the population measured at an excitation wavelength of 405 nm is about 3,000,000 $cm^{-1}M^{-1}$ or greater (e.g., 3,000,000 $cm^{-1}M^{-1}$ to about 30,000,000 $cm^{-1}M^{-1}$; or about 5,000,000 $cm^{-1}M^{-1}$ to about 20,000,000 $cm^{-1}M^{-1}$; or about 8,000,000 $cm^{-1}M^{-1}$ to about 15,000,000 $cm^{-1}M^{-1}$), wherein the population has a maximum fluorescence emission wavelength less than about 620 nm.

For any of the nanocrystal populations described herein, the nanocrystal volume to core volume ratio can be less than 100:1; or less than 99:1; or less than 98:1; or less than 97:1; 96:1; or less than about 95:1. In certain embodiments, the nanocrystal volume to core volume ratio is about 10:1 to about 25:1; or about 25:1 to about 75:1; or about 75:1 to about 95:1. In certain embodiments, greater than 75% of the nanocrystals in the population can have a nanocrystal volume to core volume ratio of 10:1 or greater. In certain embodiments, greater than 80%; or greater than 85%; or greater than 90% of the nanocrystals in the population have a nanocrystal volume to core volume ratio of 10:1 or greater. In certain embodiments, greater than 75% of the nanocrystals in the population can have a nanocrystal volume to core volume ratio of 5:1 or greater. In certain embodiments, greater than 80%; or greater than 85%; or greater than 90% of the nanocrystals in the population have a nanocrystal volume to core volume ratio of 5:1 or greater. In certain embodiments, the nanocrystal population can have a nanocrystal volume to core volume ratio of 9.1:1 or greater; 9.2 or greater; 9.3 or greater; 9.4 or greater; 9.5 or greater; 9.6 or greater; 9.7 or greater; 9.8; or greater; or 9.9 or greater.

For any of the nanocrystal populations described herein, $A_{405\ nm}/A_{band-edge}$ and/or $A_{405\ nm}/A_{(\lambda em-25\ nm)}$ can be about 150 or less; or about 30-50; or about 50-70; or about 70-90; or about 90-110; or about 110-130; or about 130-150.

For any of the nanocrystal populations described herein, each nanocrystal in the population of nanocrystals can have an average diameter of less than about 15 nm. In certain embodiments, greater than about 75% of the population of nanocrystals can have average diameters of less than about 15 nm. In certain embodiments, the average diameters can be about 3 nm to about 10 nm; or about 4 nm to about 9 nm. In certain embodiments, greater than 80%; or greater than 85%; or greater than 90% of the population can have average diameters of less than about 15 nm (or about 3 nm to about 10 nm; or about 4 nm to about 9 nm).

For any of the nanocrystal populations described herein, the average core volume of each nanocrystal can be about or about 50 $nm^3$ or less; about 100 $nm^3$ or less; or less than about 150 $nm^3$; or about 5 $nm^3$ to about 50 $nm^3$; or about 50 $nm^3$ to about 100 $nm^3$, and/or the average nanocrystal volume can be about 150 $nm^3$ or greater; or about 150 $nm^3$ to about 350 $nm^3$; or about 150 $nm^3$ to about 200 $nm^3$; or about 200 $nm^3$ to about 250 $nm^3$; or about 250 $nm^3$ to about 300 $nm^3$.

For any of the nanocrystal populations described herein, the extinction coefficient of the population measured at an excitation wavelength of 405 nm can be about 3,000,000 $cm^{-1}M^{-1}$ or greater; or about 30,000,000 $cm^{-1}M^{-1}$ or less; or about 3,000,000 $cm^{-1}M^{-1}$ to about 10,000,000 $cm^{-1}M^{-1}$; or about 10,000,000 $cm^{-1}M^{-1}$ to about 15,000,000 $cm^{-1}M^{-1}$; or about 15,000,000 $cm^{-1}M^{-1}$ to about 20,000,000 $cm^{-1}M^{-1}$; or about 20,000,000 $cm^{-1}M^{-1}$ to about 25,000,000 $cm^{-1}M^{-1}$; and/or about 25,000,000 $cm^{-1}M^{-1}$ to about 30,000,000 $cm^{-1}M^{-1}$.

The nanocrystal populations described herein can have a maximum fluorescence emission wavelength below the red spectral region; or less than about 620 nm; or in the red spectral region; or in the orange spectral region; or in the yellow spectral region; or in the green spectral region; or in the blue spectral region; or in the near-IR spectral region. These nanocrystal populations described herein when irradiated can emit light in a spectral range of no greater than about 40 nm full width at half maximum (FWHM); or no greater than about 30 nm full width at half maximum (FWHM); or no greater than about 25 nm full width at half maximum (FWHM). These nanocrystal populations described herein can exhibit minimal intermittent blinking. For example, the population can have an $\alpha_{ON}$ value of less than 1.7 or an $\alpha_{ON}$ value of less than 1.5. These nanocrystal populations described herein can be capable of undergoing FRET with donor moieties or acceptor moieties, wherein the population of nanocrystals has a FRET efficiency of greater than 20%. These nanocrystal populations can exhibit a QY of about 40% or greater; or about 60% or greater; or about 80% or greater; or about 90% or greater when measured in an organic medium or an aqueous medium. In certain embodiments, the nanocrystals in the population include a hydrophilic overcoating on the semiconductor shell that renders the nanocrystal dispersible in an aqueous medium, and the population exhibits a QY of about 40% or greater and/or an extinction coefficient of about 3,000,000 $cm^{-1}M^{-1}$ or greater when of the population when measured at an excitation wavelength of 405 nm.

In any of the nanocrystal populations described herein, the semiconductor shell can be an external layer disposed on the semiconductor core and can include one or more monolayers of semiconductor material. Any of the nanocrystals described herein can further include an intermediate semiconductor shell. An intermediate semiconductor shell layer(s) can be disposed on the semiconductor core and between the core and the external shell layer, wherein the intermediate and external shells layers are different, and can include one or more monolayers of semiconductor material. The external shell and intermediate shell, if present, can be in the form of a substantially concentric overcoating that surrounds the core. The external and/or intermediate shell, if present, can include a Group II-VI, Group II-II-VI, or Group II-VI-VI semiconductor material. For example, external and/or intermediate semiconductor shells can include CdS, ZnS, ZnCdS, ZnSeS or ZnCdSe.

At least a portion of the external shell or intermediate shell (if present) can include 3 monolayers to about 16 monolayers of semiconductor material; or about 3 monolayers to about 6 monolayers of semiconductor material; or about 6 monolayers to about 10 monolayers of semiconductor material; or about 10 monolayers to about 16 monolayers of semiconductor material. In certain embodiments, at least a portion of the external shell layer includes about 11 monolayers; or about 12 monolayers; or about 13 monolayers; or about 14 monolayers; or 15 monolayers; or 16 monolayers; or 17 monolayers; or 18 monolayers; or 19 monolayers of semiconductor material.

The semiconductor core of a nanocrystal in any of the populations described herein can include at least one Group II and at least one Group VI element. For example, the core can include a Group II-VI, a Group II-VI-VI, or a Group II-II-VI semiconductor material. The core can include a Group II-VI semiconductor material, the intermediate shell includes a Group II-II-VI or Group II-VI-VI semiconductor material, and the external shell includes a Group II-VI semiconductor material (e.g., CdSe, CdTe, CdSeTe). The core can include a semiconductor material selected from MgS, MgSe, MgTe, CaS, CaSe, CaTe, CdSe, ZnS, ZnSe, ZnTe, CdS, CdZnSSe, MgS, MgSe, MgTe, CdTe, HgS, HgSe, and HgTe. The core can include at least one Group III element and at least one Group V element (e.g., GaAs, InGaAs, InP, InAs, and InGaP).

A nanocrystal in any of the populations described herein can further include a hydrophilic (e.g., organic) overcoating on the semiconductor shell that renders the nanocrystal dispersible in an aqueous medium. This hydrophilic overcoating can include, for example, one or more amphiphilic polymers or a ligand that includes one or more thiol, amine, or phosphonate functional groups. Further, the nanocrystal in any of the populations described herein can include a linking agent capable of linking the nanocrystal to an affinity molecule or is linked to an affinity molecule. The affinity molecule can be a biological molecule such as a protein, antibody, nucleic acid (e.g., DNA, RNA, oligonucleotide or nucleotide), peptide, polypeptide, carbohydrate, or the like.

Also provided here are compositions that include the novel semiconductor nanocrystals described herein and methods of using such compositions. The composition can be a dispersion of nanocrystals. The dispersion includes a population of nanocrystals as described herein; and an aqueous or organic medium. The organic medium can include an organic solvent or a polymer. The aqueous medium can include water, buffer, saline, or any type of biologically compatible fluid. Because the nanocrystals provided herein do not dim significantly when dispersed in an aqueous medium (e.g., deionized water, borate buffer, carbonate buffer, or phosphate buffer), even at low concentrations or upon prolonged exposure to aqueous solvents, these nanocrystals also can be used in various biological applications. Nanocrystals provided herein also can be used in non-biological applications. For example, nanocrystals, as provided herein, can be included as a component in a photovoltaic or light-emitting (e.g., electroluminescent) device such as a light emitting diodes (LEDs) and solar panels. In one embodiment, nanocrystals are suspended in a medium (e.g., aqueous or non-aqueous carrier) and can be used as a fluorescent ink.

Also provided herein are kits and methods of using populations of nanocrystals. Thus, in yet another aspect, a kit for labeling cells with a population of nanocrystals is provided that includes: a) an aqueous dispersion of nanocrystals as described above; and optionally b) instructions for labeling cells with the population of nanocrystals.

In yet another aspect, a method of detecting a target species in a sample is provided that includes: contacting a sample suspected of containing a target species with a population of nanocrystals as described herein for a time sufficient to bind the target species to at least one nanocrystal in the population; and monitoring fluorescence emission to detect the presence of the at least one nanocrystal. The target species can be a biological molecule, such as, a nucleic acid, antibody, protein, peptide, carbohydrate, or the like.

In yet another aspect, a method of imaging cells or tissue with a population of nanocrystals is provided that includes: contacting cells or tissue with a population of nanocrystals as described herein for a time sufficient to label the cells or tissue with the nanocrystals; and detecting the fluorescence emission of the nanocrystals. Such methods can be used to detect the presence and location of the nanocrystals within the cells or tissue or can be used to quantify the nanocrystals present in the cells or tissue.

The methods described above can further include imaging the sample, cells or tissue to detect the presence and location of the nanocrystals. The methods can include detecting the fluorescence emission of the nanocrystals by flow cytometry. The methods also can further include quantifying the nanocrystals in the sample, cells or tissue.

In yet another aspect, methods for producing a population of nanocrystals is provided. A representative method is provided that includes:

providing a reaction mixture including a plurality of semiconductor nanocrystal cores and at least one solvent;

adding to the reaction mixture a first semiconductor shell precursor and a second semiconductor shell precursor; wherein the first and second semiconductor shell precursors are different; and heating the reaction mixture during addition of the first and second shell precursors for a period of time sufficient to induce formation of a first semiconductor shell on each of the plurality of nanocrystal cores, wherein the thickness of the shell is such that the nanocrystal volume to core volume ratio ($V_{core+shell}/V_{core}$) is 10:1 or greater.

The method can further include halting the reaction before the nanocrystal volume to core volume ratio reaches 100:1. In certain methods, the reaction is halted before the nanocrystal volume to core volume ratio reaches 99:1; or 98:1; or 97:1; or 96:1: or 95:1; or before greater than about 75% of the population of nanocrystals exceed a diameter of 15 nm. In certain embodiments, the reaction is halted before the average diameters exceed about 3 nm to about 10 nm; or about 4 nm to about 9 nm. In certain embodiments, the reaction is halted before the greater than 80%; or greater than 85%; or greater than 90% of the population of nanocrystals exceed a diameter of about 15 nm (or about 3 nm to about 10 nm; or about 4 nm to about 9 nm).

The method is conducted in a solvent (e.g., a coordinating solvent). The reaction mixture can be heated for a time sufficient to deposit about 3 to about 16 monolayers of semiconductor shell material on at least a portion of the semiconductor core, as disclosed herein. Each nanocrystal produced by the method can have an average nanocrystal volume of about 150 $nm^3$ or greater; or about 150 $nm^3$ to about 350 $nm^3$.

The method can include heating the reaction mixture during addition of the shell precursors from a first temperature to a second temperature, wherein the second temperature is greater than the first temperature. The method can further include adding the first shell precursor alternately with the second shell precursor in layer additions to form the first semiconductor shell layer on each of the plurality of nanocrystal cores. The method can further include adding a third shell precursor to the reaction mixture, wherein the first, second, and third shell precursors are added to the reaction mixture in layer additions to form the first semiconductor shell layer on each of the plurality of nanocrystal cores, wherein the first, second, and third semiconductor shell precursors are different. The method can further include adding a second semiconductor shell layer on the first semiconductor shell layer, wherein the first and second semiconductor shell layers have different compositions. In certain methods, a first shell precursor is added concurrently or alternately with a second shell precursor in layer additions to form the second shell layer. In any of the methods described herein, the first and second shell precursors are added concurrently.

The maximum emission wavelength of the population of nanocrystals can be monitored during the course of the reaction, and the reaction can be halted before the population of nanocrystals exhibits a maximum fluorescence emission wavelength of 620 nm.

The method can utilize semiconductor nanocrystal cores having a maximum emission wavelength of about 450 nm to about 550 nm; or about 460 nm to about 540 nm; or about 470 nm to about 530 nm. The nanocrystal cores can have an average core volume of less than about 150 nm$^3$; or about 100 nm$^3$ or less; or about 50 nm$^3$ or less; or about 5 nm$^3$ to about 50 nm$^3$; or about 50 nm$^3$ to about 100 nm$^3$. The semiconductor core can include at least one Group II and at least one Group VI element (e.g., a Group II-VI, a Group II-VI-VI, or a Group II-II-VI semiconductor material). The core can include a semiconductor material selected from MgS, MgSe, MgTe, CaS, CaSe, CaTe, CdSe, ZnS, ZnSe, ZnTe, CdS, CdZnSSe, MgS, MgSe, MgTe, CdTe, HgS, HgSe, and HgTe. The core can include CdSe, CdTe, or CdSeTe. The core can include at least one Group III element and at least one Group V element (e.g., GaAs, InGaAs, InP, InAs, and InGaP).

The first semiconductor shell precursor and the second semiconductor shell precursor can include an element selected from Group 12 and Group 16 elements. For example, the first semiconductor shell precursor and the second semiconductor shell precursor can include Cd, Zn, S, Se or a mixture thereof. The method can produce Group II-VI, Group II-II-VI, or Group II-VI-VI semiconductor shell (e.g., CdS, ZnS, ZnCdS, ZnSeS, or ZnCdSe). Where the method utilizes a third semiconductor shell precursor, this third semiconductor shell precursor can include a Group 16 element. In certain methods, the third semiconductor shell precursor includes S, Se, O, Te, a halogen (e.g., F), or a pnictide (e.g., N, P, As, Sb). The method can further include adding a zirconia, titania, silica, ZnS, ZnO, or MgO shell layer on the semiconductor shell.

In certain methods, an additive can be added to the reaction mixture prior to adding the first and second semiconductor shell precursors. The additive can include an element present in the semiconductor nanocrystal cores (e.g., a Group 2 element, a Group 12 element, Group 13 element, a Group 14 element, a Group 15 element, or Group 16 element). In certain embodiments, the additive can be Fe, Nb, Cr, Mn, Co, Cu, Ni, Ti, Zr, or a rare earth metal.

Also provided herein is a population of nanocrystals, wherein the nanocrystals are prepared according to any of the methods described herein. Nanocrystals prepared by the methods described herein can possess any of the structures and properties described above.

These and other features, aspects, and embodiments are described herein.

DETAILED DESCRIPTION

Figure 1:
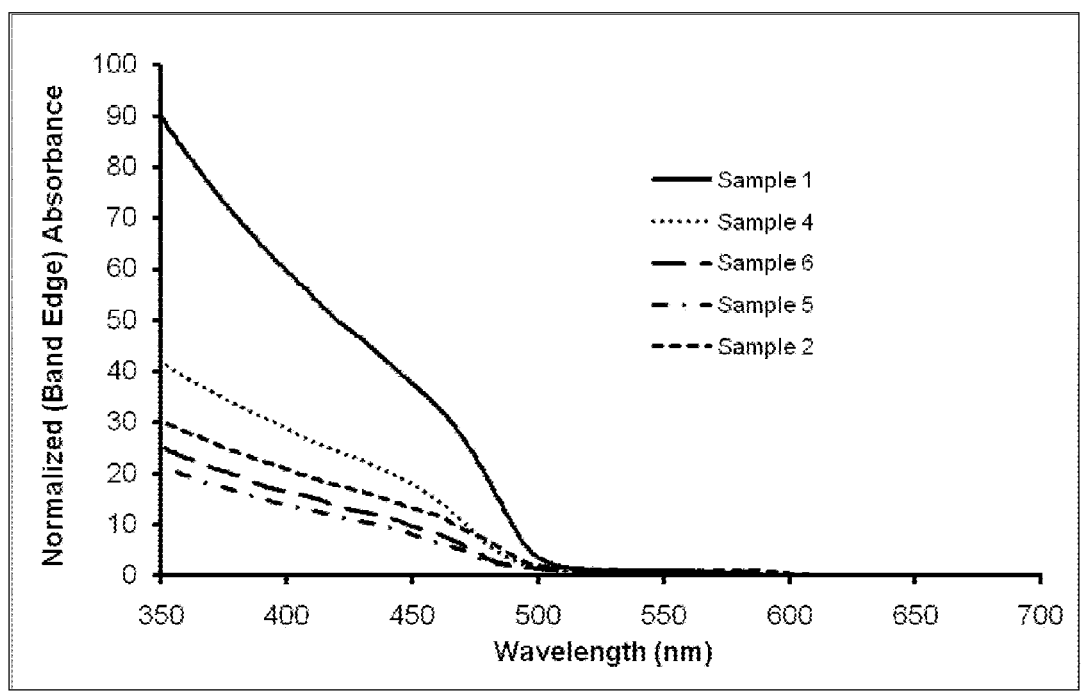
FIG. 1 is a plot of normalized absorbance spectra for various nanocrystal preparations described herein.

The embodiments described herein may be understood more readily by reference to the following detailed description of the embodiments and the Examples included herein. It is to be understood that the terminology used herein is for the purpose of describing specific embodiments only and is not intended to be limiting.

The entirety of each patent, patent application, publication and document referenced in this disclosure is hereby incorporated by reference in its entirety, including all tables, drawings, and figures.

Unless defined otherwise, all technical and scientific terms used herein have the same meaning as is commonly understood by one of ordinary skill in the art.

As used herein, "a" or "an" means "at least one" or "one or more."

As used herein, "about" means that the numerical value is approximate and small variations would not significantly affect the use and practice of the compositions and methods provided herein. Where a numerical limitation is used, unless indicated otherwise by the context, "about" means the numerical value can vary by ±10% and remain within the scope of the disclosed embodiments.

"Nanocrystal" or "nanocrystal particle" as used herein refers to a particle with at least on major dimension in the nanosize range (about 1 nm to about 1000 nm in its largest dimension) and formed of an inorganic substance that has an ordered crystalline structure. A nanocrystal can be made from a material that in the bulk is a semiconductor or insulating material and which has a tunable photophysical property in the near ultraviolet (UV) to far infrared (IR) range. A nanocrystal made from such a material is referred to herein as a "semiconductor nanocrystal" or "semiconductive nanocrystal." A nanocrystal can include a core that is made of a crystalline material, such as a semiconductor material, and the nanocrystal core can be surrounded by one or more external shell layers formed of one or more types of insulating or semiconductor materials. A semiconductor nanocrystal to which no shell has been applied is referred to herein as a "core nanocrystal" or "semiconductor core nanocrystal," whereas a semiconductor nanocrystal core with a semiconductor shell is referred to herein as a "core/shell nanocrystal" or "semiconductor core/shell nanocrystal" A nanocrystal, such as a core or core/shell nanocrystal, can be associated with an organic coating or ligands or other material on the surface of the particle, e.g., trioctylphosphine (TOP), trioctylphosphine oxide (TOPO), oleic acid, octylphosphonic acid (OPA), ethylphosphonic acid (EPA), tetradecylphosphonic acid (TDPA), or other material that is not removed from the surface by ordinary solvation. In certain embodiments, the organic coating or a layer of ligands on the particle surface is cross-linked. These surface coatings or layers can modify the properties of the particle, for example, increasing or decreasing solubility in water or other solvents.

"Water-soluble" or "water-dispersible" is used herein to mean the item can be soluble or does not aglomerate in aqueous conditions, such as in water or water-based solutions or buffer solutions, including those used in biological or molecular detection systems as known by those skilled in the art. While water-soluble nanocrystals are not truly 'dissolved' in the sense that term is used to describe individually solvated small molecules, they are solvated (via hydrogen, electrostatic or other suitable physical/chemical bonding) and suspended in solvents that are compatible with their outer surface layer, thus a nanocrystal that is readily dispersed in water is considered water-soluble or water-dispersible. A water-soluble nanocrystal can also be considered hydrophilic, since its surface is compatible with water and with water solubility.

"Hydrophilic" as used herein refers to a surface property of a solid, or a bulk property of a liquid, where the solid or liquid exhibits greater miscibility or solubility in a polar medium (e.g., water) than it does in a non-polar medium. By way of example, a material that is more soluble in methanol than in a hydrocarbon solvent such as decane would be considered hydrophilic.

"Coordinating solvents" as used herein refers to a solvent, which is effective to coordinate to the surface of a nanocrystal. 'Coordinating solvents' often include heteroatoms such as O, S, N or P to coordinate to a nanocrystal surface and include phosphines, phosphine oxides, phosphonic acids, phosphinic acids, amines, and carboxylic acids, which are often used in growth media for nanocrystals, and which form a coating or layer on the nanocrystal surface. Coordinating solvents exclude hydrocarbon solvents such as hexanes, toluene, hexadecane, octadecene, and the like, which do not have heteroatoms that provide bonding pairs of electrons to coordinate with the nanocrystal surface. Hydrocarbon solvents that do not contain heteroatoms such as O, S, N or P to coordinate to a nanocrystal surface are referred to herein as non-coordinating solvents. Note that the term 'solvent' is used in its ordinary way in these terms: it refers to a medium that supports, dissolves, or disperses materials and reactions between them, but which does not ordinarily participate in or become modified by the reactions of the reactant materials. However, in certain instances, the solvent can be modified by the reaction conditions. For example, TOP may be oxidized to TOPO, or a carboxylic acid can be reduced to an alcohol.

"Population" as used herein refers to a plurality of nanocrystals or nanocrystals having similar physical and/or optical properties. "Population" can refer to a solution or structure with more than one nanocrystal or nanocrystal at a concentration suitable for single molecule analysis. In some embodiments, the population can be monodisperse and can exhibit less than at least 15% rms deviation in diameter of the nanocrystals, and spectral emissions in a narrow range of no greater than about 75 nm full width at half max (FWHM).

As used herein, "FRET" or "fluorescence (or Förster) resonance energy transfer" refers to a process by which a fluorophore (the donor) in an excited state transfers its energy to a proximal molecule (the acceptor) by nonradiative dipole-dipole interaction (Förster, T. "Intermolecular Energy Migration and Fluorescence", *Ann. Phys.*, 2:55-75, 1948; Lakowicz, J. R., Principles of Fluorescence Spectroscopy, 2nd ed. Plenum, New York. 367-394, 1999). FRET is the basis of various fluorescence measuring techniques that allow detection of the close proximity of two molecules or species by assessing their interaction with one another.

"FRET efficiency (E)" as used herein refers to the quantum yield of the energy transfer transition, i.e. the fraction of energy transfer event occurring per donor excitation event. Therefore, the FRET efficiency of a donor (e.g., nanocrystal) describes the maximum theoretical fraction of photon energy that is absorbed by the donor (i.e., nanocrystal) and that can then be transferred to a typical organic dye (e.g., fluoresceins, rhodamines, cyanines, and the like).

"Brightness" as used herein refers to product of a particle's quantum yield (QY) and its extinction coefficient and is dictated by the following equation:

$$\text{Brightness} = (\text{Quantum Yield}) \times (\text{Extinction Coefficient})$$

"Quantum yield" or "QY" as used herein refers to the emission efficiency of a given fluorophore assessed by the number of times that a defined event, e.g., light emission, occurs per photon absorbed by the system. Unless otherwise noted, quantum yield is measured at room temperature. In other words, a higher quantum yield indicates greater efficiency and thus greater brightness of the described nanocrystal or populations thereof.

"Extinction coefficient" as used herein refers to the molar extinction coefficient (also referred to as the "molar absorption coefficient" or "molar absorptivity") and is a measurement of how strongly a chemical species absorbs light at a given wavelength on a molar basis. The extinction coefficient ($\epsilon$) is proportional to the absorbance of a sample according to the Beer-Lambert law, $A=\epsilon c l$, where absorbance, A, of a sample is dependent on the pathlength l and the concentration c of the species. Extinction coefficients can be calculated by measuring the absorbance of a sample of known concentration (within the limits of linearity) and using Beer's law to calculate extinction coefficient. The extinction coefficient of a sample of nanocrystal cores or nanocrystal core-shells can be determined using the methods similar to that described in Yu et al. (Chem. Mater. 15:2854-2860 (2003).

Disclosed herein are bright, fluorescent nanocrystals and methods of their manufacture. Nanocrystals are provided that can emit across the UV, visible and IR spectral regions. These nanocrystals are provided with a relatively thick external shell which imparts superior optical properties to the nanocrystals. These nanocrystals are surprisingly robust in that they are simultaneously highly photostable and bright. The nanocrystals can maintain a consistent spectral emission pattern (i.e., maintain the ability to fluoresce) even when exposed to a large quantity of photons (i.e., moderate to high intensity excitation) for a long period of time. The photostability of these nanocrystals is evidenced by the reduction or elimination of photobleaching (i.e., fading) behavior seen when subjected to moderate to high intensity excitation (e.g., continuous irradiation with 405 nm laser with an approximate intensity of 1 watt per cm$^2$) for prolonged periods (e.g., at least about 20 minutes). Additionally, upon high intensity excitation, the particles can remain substantially free from photo-induced color shifting. The described nanocrystals also can exhibit extremely high extinction coefficients, consistently high quantum yield, and limited or no detectable blinking (i.e., where the nanocrystal emits light non-intermittently when subject to excitation) and are sufficiently small (e.g., ≤15 nm) for use in applications that require very small particles (e.g., cell nucleus staining or FRET). This unique combination of characteristics makes the nanocrystals disclosed herein sensitive tools for single molecule analysis and other sensitive high throughput and multiplexing applications. The superior optical properties also make the disclosed nanocrystals particularly well suited for use as highly efficient donor fluorophores in energy transfer reactions such as FRET reactions.

Further, the nanocrystals provided herein can be tuned to emit brightly in novel spectral regions (e.g., at wavelengths below about 620 nm) not previously accessible with currently available materials.

The novel spectral emission properties of the disclosed materials allow them to be used in combination with a wide array of dye acceptors for FRET applications, including dyes emitting at wavelengths shorter than the red spectral region that are more stable and easier to detect than traditional near-IR emissive dyes.

The manufacturing methods provided herein address several challenges typically associated with the production of small, bright, high-quality semiconductor nanocrystals, particularly those emitting at wavelengths below the red spectral range (e.g., emission below about 620 nm). One challenge to preparing small, bright nanocrystals capable of emitting at wavelengths shorter than the red spectral range (i.e., "bluer" emitting nanocrystals) relates to leakage of the confined exciton of the core into the shell material upon excitation of the semiconductor nanocrystal. It is well known that the emission wavelength for a semiconductor nanocrystal is a function of the nanocrystal core diameter. It is also known that smaller cores result in more confinement of the electron and more leakage of the electron wavefunction into the shell. Loss of exciton confinement generally results in redder particles. An approach typically taken to solve the issue of exciton confinement is to use a shell material that has a high enough band gap that ensures low amounts of leakage. However, higher band gap materials often have smaller lattice parameters than smaller bandgap materials. When a higher bandgap material (e.g., ZnS) is used as a shell for a lower bandgap material (e.g., CdSe), the difference in lattice parameters can lead to a higher degree of lattice-mismatch. Lattice mismatch can result in defect-rich, low-quality shells with poor optical properties. A further challenge to preparing small, bright nanocrystals relates to a phenomenon referred to as Ostwald ripening. Ostwald ripening is a process that occurs during the manufacture of semiconductor nanocrystals in which smaller particles dissolve during the course of the reaction, and the dissolved constituents become absorbed by the larger particles. As a result, this process broadens the distribution of particle sizes in the population over time. In the case of a given sample of fluorescent nanocrystals, size inhomogeneity can broaden the line-width of the ensemble emission. Since Ostwald ripening increases the number of larger (i.e., redder) particles at the expense of the smaller (i.e., bluer) particles in the population, the ensemble emission wavelength of the population shifts to longer wavelengths (i.e., lower energy). This process is especially pronounced when smaller nanocrystal core materials are utilized to prepare nanocrystals with higher energy visible or UV emission.

The present disclosure addresses various obstacles associated with the preparation of semiconductor nanocrystals that emit at wavelengths shorter (i.e., to the blue) than the red spectral region. As mentioned above, the nanocrystals described herein are provided with a relatively thick external shell. These shells can serve to minimize the lattice mismatch between core and shell and can effectively reduce leakage of excitons into the shell. It has been found that certain shell materials disclosed herein can impart small nanocrystals with remarkably high extinction coefficients (i.e., about 3,000,000 $cm^{-1}M^{-1}$ or greater). When used in conjunction with relatively small semiconductor cores, bright nanocrystals with extremely large extinction coefficients are produced with relatively small diameters (e.g., less than about 15 nm) and that are capable of emitting in the violet, blue, green, yellow, orange or UV regions of the electromagnetic spectrum. When applied to larger cores the disclosed shell materials can produce bright, stable nanocrystals that emit at longer wavelengths, e.g., in the red (e.g., greater than about 620 nm) or IR regions of the spectrum, and with extremely high quantum yields (e.g., 80% or greater when measured in organic or aqueous medium). In addition to their exceptional brightness, nanocrystals are provided herein that demonstrate suppressed blinking relative to classically blinking nanocrystals of similar composition(s) or size, and yet do not suffer from pronounced red-shift or line-broadening observed for other types of thick-shell nanocrystals (see, e.g., Chen et al., J. Am. Chem. Soc. 2008, 130, 5026-5027).

Thus, in one aspect, a fluorescent core/shell nanocrystal or populations thereof is provided that includes an optically active nanocrystalline, semiconductor core and one or more semiconductor shell layers. The semiconductor shell layer(s) typically is a substantially concentric (onion-like) overcoating that surrounds the core. The semiconductor shell can provide a physical bather between the optically active core and the surrounding medium. The shell is substantially uniform in coverage around the core and is substantially free of defects. The presence of the external shell can reduce the nanocrystal's sensitivity to environmental changes, reduce photo-oxidation, and can help passivate surface trap states to significantly enhance fluorescence quantum yield.

The nanocrystal core and shell can be made of any suitable metal and non-metal atoms that are known to form semiconductor nanocrystals. Suitable semiconductor materials for the core and/or shell include, but are not limited to, ones including Group 2-16, 12-16, 13-15 and 14 element-based semiconductors such as ZnS, ZnSe, ZnTe, CdS, CdSe, CdTe, HgS, HgSe, HgTe, MgS, MgSe, MgTe, CaS, CaSe, CaTe, SrS, SrSe, SrTe, BaS, BaSe, BaTe, GaN, GaP, GaAs, GaSb, InP, InAs, InSb, AlAs, AlP, AlSb, PbS, PbSe, Ge and Si and mixtures thereof. In some embodiments, the core and the shell of a core/shell nanocrystal are composed of different semiconductor materials, meaning that at least one atom type of a semiconductor material of the core of a core/shell is different from the atom types in the shell of the core/shell nanocrystal.

In certain embodiments, the core includes a mixture of at least one Group II element and at least one Group VI element (e.g., CdSe or CdTe or a mixture thereof) or a Group II-VI-VI, or a Group II-II-VI semiconductor material. In other embodiments, the core includes a mixture of at least one Group III element and at least one Group V element (e.g., GaAs, InGaAs, InP, InAs, or InGaP or a mixture thereof).

Suitable materials for the shell typically include a semiconductor material having a higher bandgap energy than that of the semiconductor nanocrystal core, however, other arrangements are also possible. In addition to having a bandgap energy greater than the semiconductor nanocrystal core, suitable materials for the shell can in certain embodiments have good conduction and valence band offset with respect to the core semiconductor nanocrystal. Thus, the conduction band is desirably higher and the valence band is desirably lower than those of the core semiconductor nanocrystal. The shell and core materials are typically chosen to minimize lattice mismatch. For semiconductor nanocrystal cores that emit energy in the visible (e.g., CdS, CdSe, CdTe, ZnS, ZnSe, ZnTe, GaP, GaAs, GaN) or near IR (e.g., InP, InAs, InSb, PbS, PbSe), a material that has a bandgap energy in the ultraviolet regions may be used. Exemplary materials include CdS, CdSe, InP, InAs, ZnS, ZnSe, ZnTe, GaP, GaN, and magnesium chalcogenides, e.g., MgS, MgSe, and MgTe. For a semiconductor nanocrystal core that emits in the near IR, materials having a bandgap energy in the visible, such as CdS or CdSe, may also be used. It is also understood in the art that the actual fluorescence wavelength for a particular nanocrystal core depends upon the size of the core as well as its composition, so the categorizations above are approximations, and nanocrystal cores described as emitting in the visible or the near IR can actually emit at longer or shorter wavelengths depending upon the size of the core.

The shell can take a variety of forms and can be a multi-layer shell or an alloyed shell. In one construction, the nanocrystal or populations thereof includes a core and a layered shell, wherein the shell includes m inner shell monolayers including a first shell material $(M^1X)_m$ and n outer shell monolayers including a second shell material $(M^2X)_n$, wherein M can be a metal atom and X can be a non-metal atom, each of m and n is independently an integer from 1 to 10. In specific embodiments, the sum of m+n is 3-20, or 5-14, or 6-12, or 7-10. In certain embodiments, one or more additional shell layers can reside between the at least one inner shell layer and the at least one outer shell layer.

In certain embodiments, the core includes CdSe, the at least one inner shell layer includes CdS, and the at least one outer shell layer includes ZnS. In a particular embodiment, the nanocrystal has a CdSe core and a layered shell including multiple CdS layers and multiple ZnS layers. In some embodiments, the CdSe core is overcoated with a first set of CdS layers and then overcoated with a second set of ZnS layers.

In other embodiments, alloyed shells are provided that can reduce lattice mismatch and thereby improve the nanocrystal's optical properties. These effects can be achieved without substantial red-shifting of the emission band of the core-shell nanocrystal. An "alloyed shell" refers to a shell material that includes a mixture of two or more semiconductor materials. The alloyed shell can include one or more atoms present in the core or can include materials different than those used in the core. In certain embodiments, the shell material includes an alloy of a Group II-VI or Group II-VI-VI semiconductor material, such as CdS, ZnS, ZnCdS, ZnCdSe. The atoms of the alloyed shell can be homogeneously distributed throughout the shell. Alternatively, certain materials in the alloyed shell form a compositional gradient between core and shell. For example, where the shell includes a Cd/Zn/S alloy, the concentration of Cd can be higher near the core and lower near the surface. Thus, the concentration of Cd forms a more or less smooth compositional gradient between these extremes as the distance from the semiconductive core increases. Gradient alloyed shells are provided herein that minimize the lattice mismatch resulting from certain combinations of core and shell materials. In certain embodiments, the nanocrystal further includes a further outer shell layer formed of ZnS or another type of semiconductor shell material disposed on the alloyed (intermediate) shell material.

In another construction, a nanocrystal is provided with a layered shell, wherein the shell includes sequential monolayers comprising an alloyed multi-component shell material of the form $M^1_xM^2_yX$, where $M^1$ and $M^2$ can be metal atoms and X can be a non metal atom, where the composition becomes successively enriched in $M^2$ as the monolayers of shell material are deposited, where x and y represent the ratio of $M^1$ and $M^2$ in the shell material.

In certain embodiments, the layered shell may be engineered such that the sequential monolayers are selected to provide a confining gradient potential from the nanocrystal core to the outer surface of the nanocrystal shell. The steepness of the confining potential gradient may vary depending on the nature of the shell materials selected for each monolayer or group of monolayers. For example, a nanocrystal comprising several sequential monolayers of the same shell material may reduce the potential through a series of steps, while a more continuous gradient may be achievable through the use of sequential monolayers of a multi-component alloyed shell material. In some embodiments, both single component and multi-component shell materials may be applied as different monolayers of a multi-layer shell on a nanocrystal.

The color (i.e., emitted light) of a nanocrystal can be "tuned" by varying the size and composition of the particle. Nanocrystals as disclosed herein can absorb a wide spectrum of wavelengths, and emit a relatively narrow wavelength of light. The excitation and emission wavelengths are typically different, and non-overlapping. Depending on the size of the nanocrystal core, these nanocrystal(s) can emit in the UV, visible or IR portions of the electromagnetic spectrum. The emission maxima of the disclosed nanocrystal and populations thereof can generally be at any wavelength from about 200 nm to about 2500 nm. In certain embodiments, nanocrystals are provided that emit in the UV or visible range of electromagnetic spectrum below about 620 nm (i.e., wavelengths that fall below the red spectral region). For example, the nanocrystals that emit below the red spectral region can emit below about 620 nm; or about 610 nm or less, or about 600 nm or less, or about 590 nm or less, or about 580 nm or less, or about 570 nm or less, or about 560 nm or less; or about 540 nm or less. In certain embodiments, the population of nanocrystals emits violet or indigo (e.g., about 380 nm to about 450 nm). In other embodiments, the population emits blue light (e.g., about 450 nm to about 495 nm). In other embodiments, the population emits green light (e.g., about 495 nm to about 565 nm). In yet other embodiments, the population emits yellow light (e.g., about 565 nm to about 590 nm). In yet other embodiments, the population emits orange light (e.g., about 590 nm to about 620 nm). In yet other embodiments, the population emits red light (e.g., about 620 nm to about 700 nm). In yet other embodiments, the population emits in the near-IR regions of the spectrum (e.g., between about 700 nm to about 1000 nm).

The nanocrystal(s) can have any diameter, where the diameter is measured along the shortest axis of the nanocrystal. Typically, a nanocrystal is about 1 nm to about 100 nm; or about 1 nm to about 20 nm; or about 1 nm to about 15 nm; or about 1 nm to about 10 nm; or 1 nm to about 5 nm; or about 5 nm to about 10 nm. In some such embodiments, the nanocrystals may have a smallest dimension of about 0.5 nm, about 1 nm, about 2 nm, about 3 nm, about 4 nm, about 5 nm, about 6 nm, about 7 nm, about 8 nm, about 9 nm, about 10 nm, about 11 nm, about 12 nm, about 13 nm, about 14 nm, about 15 nm, about 16 nm, about 17 nm, about 18 nm, about 19 nm, about 20 nm, about 25 nm, about 30 nm, about 35 nm, about 40 nm, about 45 nm, about 50 nm or a diameter ranging between any two of these values.

In certain embodiments of single-color preparation of the nanocrystals disclosed herein can have individual nanocrystals that are of substantially identical size and shape. Typically, nanocrystals are sized to provide fluorescence in the UV-IR portion of the electromagnetic spectrum, as this range is convenient for use in monitoring biological events in relevant media. Such a collection of particles is sometimes referred to as being a "monodisperse" population. One of ordinary skill in the art will realize that particular sizes of nanocrystals can be obtained as particle size distributions. Thus, also provided herein are populations of nanocrystals or nanocrystals where greater than 75% (e.g., greater than 80%; or greater than 85%; or greater than 90%; or greater than 95%) of the nanocrystals or nanocrystals in the population have substantially identical diameters. In such embodiments, greater than 75% of the nanocrystals or nanocrystals can have a diameter of about 20 nm or less. In other embodiments, greater than 75% of the nanocrystals or nanocrystals can have a diameter of about 15 nm or less. In certain embodiments, greater than 80%; or greater than 85%; or greater than 90%; or greater than 95% of the nanocrystals or nanocrystals can have a diameter of about 15 nm or less). In other embodiments, greater than 75% of the nanocrystals or nanocrystals can have a diameter of about 10 nm or less (e.g., 9 nm, 8 nm, 7 nm, 6 nm, or 5 nm).

In some embodiments, the size and shape between the individual nanocrystals in a population of nanocrystals should vary by no more than about 20%, no more than about 15%, no more than about 10%, no more than about 8%, no more than about 6%, no more than about 5%, no more than about 4%, no more than about 3% or less in at least one measured dimension. In some embodiments, disclosed herein is a population of nanocrystals, where at least about 60%, at least about 70%, at least about 80%, at least about 90%, at least about 95%, and ideally about 100% of the particles are of the same size. Size deviation can be measured as root mean square ("rms") of the diameter, with the population having less than about 30% rms, preferably less than about 20% rms, more preferably less than about 10% rms. Size deviation can be less than about 10% rms, less than about 9% rms, less than about 8% rms, less than about 7% rms, less than about 6% rms, less than about 5% rms, less than about 3% rms, or ranges between any two of these values.

The nanocrystal populations described herein can be characterized in that they produce a fluorescence emission having a relatively narrow wavelength band indicative of a population of similarly sized (i.e., monodisperse) nanocrystals. The width of ensemble emission band is typically less than about 60 nm full width at half maximum (FWHM), or less than about 50 nm FWHM, or less than about 40 nm FWHM, or less than about 30 nm FWHM or less than about 20 nm FWHM, when measured at room temperature. The emitted light preferably has a symmetrical (e.g., Gaussian), monomodal emission band. Certain materials provided herein exhibit astounding color purity (e.g., less than about 30 nm FWHM) indicative of a highly monodisperse population, as well as favorable optical properties (e.g., minimal intermittent blinking, high extinction coefficient, high quantum yield, photostability or a combination of two or more of these properties) even at emission wavelengths below the red spectral region.

The nanocrystals described herein can have extremely high extinction coefficients. In certain embodiments, nanocrystals with high extinction coefficients are provided that emit below the red spectral range (e.g., less than 620 nm). The extinction coefficient can be measured at various wavelengths, although it is generally most practical to use an excitation wavelength of 405 nm (the wavelength used in many commercial lasers). At this excitation wavelength, the extinction coefficient for the disclosed nanocrystal(s) typically ranges from about 3,000,000 $cm^{-1}M^{-1}$ to about 30,000,000 $cm^{-1}M^{-1}$. For example, the nanocrystals described herein can exhibit an extinction coefficient measured at an excitation wavelength of 405 nm can be about 3,000,000 $cm^{-1}M^{-1}$ to about 10,000,000 $cm^{-1}M^{-1}$; or about 10,000,000 $cm^{-1}M^{-1}$ to about 15,000,000 $cm^{-1}M^{-1}$; or about 15,000,000 $cm^{-1}M^{-1}$ to about 20,000,000 $cm^{-1}M^{-1}$; or about 20,000,000 $cm^{-1}M^{-1}$ to about 25,000,000 $cm^{-1}M^{-1}$; and/or about 25,000,000 $cm^{-1}M^{-1}$ to about 30,000,000 $cm^{-1}M$. Unexpectedly, for certain nanocrystal compositions, these high extinction coefficients can be achieved despite their small size and without the expected red-shifting of the fluorescence emission band.

The disclosed nanocrystals also exhibit a high quantum yield (i.e., ratio of photons emitted to photons absorbed). A high quantum yield can indicate that some or all of the potential non-irradiative pathways (e.g., due to surface trap states or crystalline defects) are absent in the collection of semiconductor nanocrystals sampled. Thus, quantum yield is an important measure for determining the quality of any given population of fluorescent semiconductor nanocrystals. The disclosed nanocrystals can have a quantum yield of at least about 20%, at least about 40%, at least about 50%, at least about 60%, at least about 70%, at least about 80%, at least about 90%, at least about 95%, at least about 98%. In some embodiments, provided herein is a population of nanocrystals where at least about 30%, at least about 40%, at least about 50%, at least about 60%, at least about 70%, at least about 80%, at least about 90%, at least about 95%, at least about 98%, at least about 99% or more of the nanocrystals in the population has a QY of at least about 25%, at least about 40%, at least about 50%, at least about 60%, at least about 70%, at least about 80%, at least about 90%, at least about 95%, at least about 98%, at least about 99% or more.

Quantum yield can be measured in either an aqueous or an organic medium. Certain nanocrystals (or a population thereof) provided herein exhibit a QY of about 60% or greater; or about 70% or greater; or about 80% or greater; or about 85% or greater when measured in an aqueous or organic medium.

By virtue of their high extinction coefficients and high quantum yield, nanocrystals are provided herein that are exceptionally bright. In certain embodiments, the nanocrystal(s) has a quantum yield of greater than about 80% and an extinction coefficient of about 3,000,000 $cm^{-1}M^{-1}$ to about 30,000,000 $cm^{-1}M^{-1}$, when measured at an excitation wavelength of 405 nm. In other embodiments, the nanocrystal(s) when excited at 405 nm has a quantum yield of greater than about 75% and an extinction coefficient of about 5,000,000 $cm^{-1}M^{-1}$ to about 20,000,000 $cm^{-1}M^{-1}$. In yet other embodiments, the nanocrystal(s) when excited at 405 nm has a quantum yield of greater than about 60% and an extinction coefficient of about 5,000,000 $cm^{-1}M^{-1}$ to about 15,000,000 $cm^{-1}M^{-1}$. In yet other embodiments, the nanocrystal(s) when excited at 405 nm has a quantum yield of greater than about 40% and an extinction coefficient of about 10,000,000 $cm^{-1}M^{-1}$ to about 15,000,000 $cm^{-1}M^{-1}$.

Nanocrystal brightness is often compromised during prolonged storage in solvents or as a result of quenching. Additionally, fluorescent nanocrystals can suffer from intermittent fluorescence or a stochastic blinking on and off of their fluorescence when the nanocrystals are excited. This blinking on and off limits the robustness of the signal as both the timing and duration of the on/off periods are unpredictable. For single particle or single molecule analysis, the blinking properties limit the usefulness of the fluorescent nanocrystals. Similarly, blinking results in significant hurdles in ultra high-throughput applications using a population of nanocrystals, due to unpredictable variations in signal intensity resulting from the nanocrystals intermittently toggling between an on/off state. The fluorescent nanocrystal or populations thereof provided herein can exhibit modulated, reduced or no intermittent (e.g., continuous, non-blinking) fluorescence.

The blinking behavior of the nanocrystals described herein can be analyzed and characterized by any suitable number of parameters using suitable methodologies. In some embodiments, the probability distribution function of the "on" and "off" blinking time durations (i.e., blinking behavior) can be determined using the form of an inverse power law. A value, alpha ($\alpha$) can be calculated, wherein $\alpha$ represents an exponent in the power law. As the percentage of the population that is non-blinking increases, the value of $\alpha_{on}$ theoretically approaches zero. In conventional nanocrystal populations previously described, $\alpha_{on}$ typically ranges from about 1.5 to about 2.5, under moderate to high excitation energy.

Most alpha calculations can use a predetermined threshold to determine the "on" and "off" values of alpha-on and alpha-off (i.e., $\alpha_{on}$ and $\alpha_{off}$). In some embodiments, an alpha estimator that calculates the on/off threshold for each dot individually can be employed. The data can be represented by a plot of signal versus frequency, and typically appears as a series of Gaussian distributions around the "off state" and one or more "on states." A log-log plot of frequency versus time for each period of time that the dot is "on" provides a straight line having a slope of $\alpha_{on}$. The value of alpha-off ($\alpha_{off}$) can be similarly determined.

In a specific example, the fluorescent intermittency measurements can be made using a Total Internal Reflection Fluorescence (TIRF) microscope fitted with a 60× oil immersion objective lens. Using the TIRF setup, the nanocrystals are imaged at 62 Hz (16 ms), typically for 5 minutes, to produce a movie showing the time and intensity of the emitted light for each individual spot (corresponding to a single particle) within a frame that was 16 ms long. Each data set can be manually analyzed dot-by-dot, and aggregates and other artifacts are excluded. From the edited results, the following parameters can be calculated: alpha-on ("$\alpha_{on}$"); alpha-off ("$\alpha_{off}$"); the percent on; longest on/longest off; overlap scores; and the median values for each of these parameters.

Particles can be binned into three categories: low-blinkers for which an $\alpha_{on}$ of below about 1.1 is measured; mid-blinkers for which an $\alpha_{on}$ of below 1.3 is measured, and high-blinkers for which an $\alpha_{on}$ between 1.3 and 1.5 or higher is measured. In some embodiments, provided herein is a nanocrystal or population thereof having an $\alpha_{on}$ of less than about 1.7; or $\alpha_{on}$ of less than about 1.6; or $\alpha_{on}$ of less than about 1.5; or $\alpha_{on}$ of less than about 1.4, or $\alpha_{on}$ of less than about 1.3; or $\alpha_{on}$ of less than about 1.2; or $\alpha_{on}$ of less than about 1.1, under moderate to high excitation energy. Further provided is a population of more than one nanocrystal wherein the at least about 50%, at least about 60%, at least about 70%, at least about 80%, at least about 90%, at least about 95%, at least about 98%, at least about 99% or more of the population has an $\alpha_{on}$ of less than about 1.7; or $\alpha_{on}$ of less than about 1.6; or $\alpha_{on}$ of less than about 1.5, or $\alpha_{on}$ of less than about 1.4, or $\alpha_{on}$ of less than about 1.3, or $\alpha_{on}$ of less than about 1.2, or $\alpha_{on}$ of less than about 1.1 for the time observed, under moderate to high excitation energy. For conventional core-shell nanocrystals, under an excitation rate of 150,000 photons per second, the distribution of low-medium-high blinking is typically 30%-50%. For the nanocrystals disclosed herein, under an increased excitation rate of 300,000 absorbed photons per second, the low-medium-high distribution can be about 25%-50%. The observation time can be at least about 5 minutes, at least about 10 minutes, at least about 15 minutes, at least about 30 minutes, at least about 45 minutes, at least about 60 minutes, at least about 90 minutes, at least about 120 minutes or more under moderate to high excitation energy.

Also provided herein is a nanocrystal or a population thereof having a stochastic blinking profile that is either undetectable or rare (e.g., no more than 1-2 events during the interrogation period) over an observed timescale. In this case, "undetectable" encompasses the situation in which evidence might exist for ultra-fast blinking on a timescale that is faster than the binning timescale (e.g., dimming and brightening from bin to bin) but there are no "off" events persisting for longer than the bin time. Therefore, in some embodiments, a nanocrystal or populations thereof has a stochastic blinking profile that is undetectable for at least about 50%, at least about 60%, at least about 70%, at least about 80%, at least about 85%, at least about 90%, at least about 95%, at least about 98%, at least about 99% or more of the time observed, under moderate to high excitation energy. Further provided, is a population of nanocrystals wherein at least about 50%, at least about 60%, at least about 70%, at least about 80%, at least about 90%, at least about 95%, at least about 98%, at least about 99% or more of the individual nanocrystals in the population have a stochastic blinking on a timescale that is undetectable for the time observed, under moderate to high excitation energy. The timescale can be at least about 5 minutes, at least about 10 minutes, at least about 15 minutes, at least about 30 minutes, at least about 45 minutes, at least about 60 minutes, at least about 90 minutes, at least about 120 minutes or more under moderate to high excitation energy.

In some embodiments, the longest on and longest off values can relate to the longest period of time a nanocrystal is observed to be in either the "on" or the "off" state. In particular, the longest on value can be important to determining the length of time and amount of data that may be measured in a particular assay.

Thus, the blinking characteristics of the nanocrystals herein can also be characterized by their on-time fraction, which represents the (total on-time)/(total experiment time). Referring to the TIRF example disclosed herein, the total on time can be determined by the total number of frames "on" multiplied by 16 ms, and the total experiment time is 5 minutes. For example, the blinking properties of the disclosed nanocrystals or populations thereof can be determined under continuous irradiation conditions using a 405 nm laser with an intensity of about 30 watt per cm$^2$ during an experimental window of at least 5 minutes.

On-time fractions can be used to characterize the blinking behavior of a single nanocrystal or of a population of nanocrystals. It is important to note that the on-time fraction for a particular nanocrystal or population of nanocrystals is a function of the specific conditions under which the percent of blinking or "non-blinking" nanocrystals is determined. For example, the nanocrystals or populations described herein can have an on-time fraction of at least about 0.50, at least about 0.60, at least about 0.70, at least about 0.75, at least about 0.80, at least about 0.85, at least about 0.90, at least about 0.95, at least about 0.96, at least about 0.97, at least about 0.98, or at least about 0.99 or more, under moderate to high excitation energy. In some embodiments, a nanocrystal or populations thereof having a percent on-time of about 98%, about 99% (i.e., on-time fraction of about 0.99) can be considered to be "non-blinking." (e.g., blinking is modulated), under moderate to high excitation energy. At least about 50%, at least about 60%, at least about 70%, at least about 80%, at least about 90%, at least about 95%, at least about 98%, at least about 99%, or more of the individual nanocrystals in a population of nanocrystals can have an on-time fraction of at least about 0.50, at least about 0.60, at least about 0.70, at least about 0.75, at least about 0.80, at least about 0.85, at least about 0.90, at least about 0.95, at least about 0.96, at least about 0.97, at least about 0.98, or at least about 0.99 or more, under moderate to high excitation energy. The on-times of the nanocrystals are typically for at least about 5 minutes, at least about 10 minutes, at least about 15 minutes, at least about 20 minutes, at least about 30 minutes, at least about 45 minutes, at least about 60 minutes, at least about 70 minutes, at least about 80 minutes, at least about 90 minutes, at least about 120 minutes under moderate to high intensity excitation of the nanocrystal or nanocrystal population. Under one set of conditions, continuous irradiation with 405 nm laser with an approximate intensity of 30 watt per $cm^2$ was used to determine the stochastic blinking profile.

In some embodiments, nanocrystals may blink on and off on a timescale that is too rapid to be detected under the methods employed to study this behavior. Thus, certain nanocrystals can effectively appear to be "always on" or to have on-time fractions of about 0.99, when in fact they flicker on and off at a rate too fast or too slow to be detected. Such flickering has relatively little impact on the performance of a system, and for practical purposes such nanocrystals can be considered to be non-blinking.

In some instances, the disclosed nanocrystals and populations thereof are not observed to blink off under the analysis conditions, and such particles can be assessed as "always on" (e.g., non-blinking). The percent of usable dots that are "always on" can be a useful way to compare nanocrystals or populations of nanocrystals. However, a determination of "always on" may mean that the "off" time is insufficient to provide enough a signal gap for accurate determination and thus the value in the regime of particles is insufficient to calculate. Even these "non-blinking" nanocrystals may flicker on and off on a timescale that is not detected under the conditions used to assess blinking. For example, certain particles may blink on a timescale that is too fast to be detected, or they may blink very rarely, and, in some embodiments, such particles may also be considered to be "always-on" or non-blinking, as the terms are used herein.

In some embodiments, a nanocrystal or populations thereof may demonstrate some fluctuation in fluorescence intensity. Typically, the change in fluorescence intensity for a nanocrystal is less than about 5%, less than about 10%, less than about 20%, or less than about 25% of the nanocrystal or populations thereof at its greatest intensity, under moderate to high excitation energy. Similarly, in a population of nanocrystals, such changes in fluorescence intensity of less than about 5%, less than about 10%, less than about 20%, or less than about 25% of the highest intensity can occur in for at least about 50%, at least about 60%, at least about 70%, at least about 80%, at least about 85%, at least about 90%, at least about 95%, at least about 98%, at least about 99% of the nanocrystals in the population, under moderate to high excitation energy.

The nanocrystals (and populations thereof) provided herein can act as either a donor or acceptor in a FRET reaction. Nanocrystals that can undergo a measurable FRET energy transfer event with an acceptor or donor moiety are referred to herein as "FRET capable." In a FRET reaction, a donor moiety can non-radiatively transfer energy to an acceptor moiety. The acceptor can be a chromophore or fluorophore which can then emit a photon. In some applications, the acceptor can also be a quencher. Donor-acceptor pairs are selected such that there is overlap between the emission spectrum of the donor and excitation spectrum of the acceptor. In certain embodiments, the nanocrystals are particularly well suited for use as a donor that undergoes FRET with a suitable acceptor moiety (e.g., fluorescent dyes, etc.).

Nanocrystals are provided herein that exhibit high FRET efficiency and thus are excellent partners (e.g., donors) in a FRET reaction. FRET efficiency can depend sharply on donor-acceptor distance R as $1/R^6$. The distance where FRET efficiency is 50% is termed $R_0$, also known as the Förster distance. $R_0$ can be unique for each donor-acceptor combination and can range from about 5 nm to about 10 nm. In biological applications, FRET can provide an on-off type signal, indicating when the donor and acceptor are within $R_0$ of each other. Thus, the overall size (diameter) of the nanocrystal can significantly impact the maximum theoretical limit of its FRET efficiency (i.e., FRET efficiency) with an acceptor moiety. As such, in general, most FRET capable nanocrystals have a diameter that is than about 40 nm, less than about 30 nm, less than about 20 nm, and preferably less than about 15 nm or less than about 10 nm (inclusive of any surface treatments or coatings covering the exterior of the nanocrystal). Additional factors affecting FRET efficiency can include the quantum yield of the donor, the extinction coefficient of the acceptor, the degree of spectral overlap between donor and acceptor, and characteristics of the core/shell materials and external coatings.

A nanocrystal or populations thereof is provided herein with a FRET efficiency of at least about 20%, at least about 40%, at least about 50%, at least about 60%, at least about 70%, at least about 80%, at least about 90%, at least about 95%, at least about 98%, at least about 99%, or greater up to 100%. A FRET capable nanocrystal typically has at least about 20% efficiency in a FRET reaction.

As discussed above, the nanocrystals provided herein can be surprisingly photostable. In particular, these nanocrystal(s) can be photostable over an extended period of time while maintaining the ability to effectively participate in energy transfer (i.e., FRET) reactions. As such, in some embodiments, photostable nanocrystals are provided having FRET efficiencies of at least about 20%. The disclosed nanocrystals can be stable under high intensity conditions involving prolonged or continuous irradiation over an extended period of time from a moderate to high excitation source. Photostable, FRET capable nanocrystals are particularly useful for many applications involving the real-time monitoring of single molecules.

There are various other objective indicia of nanocrystal photostability. For example, a nanocrystal can be classified as photostable when the nanocrystal, under moderate to high excitation, emits about 1,000,000 to about 100,000,000 photons or more preferably about 100,000,001 to about 100,000,000,000 photons or even more preferably more than about 100,000,000,000 photons before becoming non-emissive (i.e., bleached).

The disclosed nanocrystal and populations of such nanocrystals can have any combination of the properties described herein. Thus, further provided herein are compositions comprising a population of nanocrystals, wherein at least about 10%, at least about 20%, at least about 30%, at least about 40%, at least about 50%, at least about 60%, at least about 70%, at least about 80%, at least about 90%, and at least about 95% of the nanocrystals have at least one of the properties or characteristics disclosed herein.

The nanocrystals described herein include relatively thick shells in comparison to the size of the cores and/or overall nanocrystal dimensions. The shell thickness can vary depending on the type of semiconductor materials and the desired optical properties of the resulting nanocrystal. The external shell can have the same thickness over the entire particle or it can vary in thickness. For example, for a rod-shaped particle, the shell thickness along the short axis can be less than at either end of the particle.

The thickness of the semiconductor shell can be measured directly using techniques well known in the art such as transmission electron microscopy (TEM). Alternatively, shell thickness can be estimated based on the amounts of reagents utilized in the synthesis procedure. In certain embodiments, the external shell is about 5 nm to about 40 nm in thickness; typically about 5 nm to about 20 nm. The shell thickness can be expressed in terms of monolayers of semiconductor material. Generally, the number of monolayers of shell material is adjusted to avoid any unnecessary red-shifting of the nanocrystal emission wavelength. Depending on the type of and/or shell materials and the shell construction, the external shell typically includes greater than 5 monolayers of semiconductor material. Typically, the shell includes less than 20 monolayers of semiconductor shell material, or less than 19 monolayers of shell material; or less than 18 monolayers of shell material; or less than 17 monolayers of shell material; or less than 16 monolayers of shell material. In certain embodiments, the shell is provided with greater than 5 monolayers; and typically about 6-18 monolayers; or about 7-17 monolayers; or about 8-16 monolayers; or about 9-15 monolayers of semiconductor shell material.

In yet another method, the thickness of the shell can be expressed in terms of volume. The nanocrystals (e.g., core/shell nanocrystals) can be described using a ratio of the volume of the nanocrystal (which includes the contribution of the core and the shell) to the volume of the core.

$$(V_{core+shell}/V_{core})$$

This ratio of volumes (also referred to herein as a "shell: core" volume ratio) provides valuable information about the total amount and thickness of shell overcoating material deposited on the core, without needing to assume that the thickness of the shell overcoating is uniform about the core of the particle.

The volume calculated for the core-shell nanocrystal depends on the overall shape of the particle. When the nanocrystal(s) includes a shell, the overall volume of the nanocrystal is dictated by the final shape of the shell overlaying the core material. The semiconductor nanocrystal(s) described herein can take any shape, however, frequently are in the form of spheres or ellipsoids. Thus, a rod-shaped core can be overcoated with a shell resulting in a spherically-shaped core/shell nanocrystal. Conversely, a spherical core can be overcoated with a shell resulting in a rod-shaped core/shell nanocrystal. When the nanocrystal has a generally spherical shape, its volume can readily be calculated using the volume equation for a sphere. The volume of particles having an elongated structure can be calculated to close approximation using the volume equation for an ellipsoid. Formulae and techniques for calculating the volume of spheres, ellipsoids, and other three-dimensional shapes are well known to those in the art. The core-shell nanocrystal(s) volume (i.e., the overall volume) is generally less than about 300 nm$^3$ (e.g., less than 250 nm$^3$; or less than 200 nm$^3$; or less than about 150 nm$^3$; or less than about 100 nm$^3$ or less than about 50 nm$^3$). Certain core-shell nanocrystals described herein have a volume of about 100 nm$^3$ to about 350 nm$^3$; or about 100 nm$^3$ to about 150 nm$^3$; or about 150 nm$^3$ to about 200 nm$^3$; or about 200 nm$^3$ to about 250 nm$^3$; or about 250 nm$^3$ to about 300 nm$^3$; or about 300 nm$^3$ to about 350 nm$^3$ The volume ratio also depends on the volume of the semiconductor core. The nanocrystals described herein also are characterized by relatively small cores relative to the size of the overall core-shell nanocrystal. Semiconductor nanocrystals with relatively small cores (e.g., CdSe) are known to exhibit fluorescence emission in the visible or UV portions of the electromagnetic spectrum, while larger cores often emit in the near-IR to IR regions of the spectrum. Typical core sizes range in size depending on the desired emission color and typically range from about 1-10 nm in diameter (along the shortest dimension). For nanocrystals that emit below the red spectral range, the core size is about typically about 1 to about 5 nm. In certain embodiments, such nanocrystal cores can emit light between about 440 nm to about 550 nm. For nanocrystal cores that emit in the red or near-IR spectral range, the core size can be about 4-10 nm (along the shortest dimension).

The semiconductor core can have any shape. Cores frequently are in the form of spheres. However, non-spherical cores are also common. Non-spherical cores have an elongated profile that can be characterized in terms of an aspect ratio, where a non-spherical core has an aspect ratio of greater than 1:1 (e.g., 10:1 or less). Such non-spherical cores can be in the form of, for example, ellipsoids or rods. When the core has a generally spherical shape, its volume can readily be calculated using the volume equation for a sphere. The volume of a core having an elongated structure can be calculated to close approximation using the volume equation for an ellipsoid. The core nanocrystal(s) volume is generally less than about 150 nm$^3$; or less than about 100 nm$^3$; or less than about 50 nm$^3$; or less than about 25 nm$^3$. In certain embodiments, the core volume is between about 5 nm$^3$ to about 25 nm$^3$; or about 5 nm$^3$ to about 20 nm$^3$.

The nanocrystal volume to core volume ratio typically has a value greater than about 5:1 but less than about 100:1 (e.g., 99:1; or 98:1; or 96:1; or 95:1). In certain embodiments, the ratio of nanocrystal to core volume ranges from about 5:1 to about 10:1. In other embodiments where the core has a volume ratio as described above, the ratio of nanocrystal to core volume ranges from about 10:1 to about 20:1; or about 20:1 to about 50:1; or about 50:1 to about 80:1; or about 80:1 to about 95:1. Nanocrystals having volume ratios ranging from about 10:1 to about 95:1 are provided herein that emit below the red spectral range (e.g., less than 620 nm; or less than 610 nm; or less than 600 nm; or less than 590 nm; or less than 580 nm).

Core-shell nanocrystals have such volume ratios can be produced using many core/shell combinations. In certain embodiments, the core can have a diameter of about 1-10 nm, such that the core nanocrystal volume is generally less than about 150 nm$^3$; or less than about 100 nm$^3$; or less than about 50 nm$^3$; or less than about 25 nm$^3$; or less than about 10 nm$^3$. In certain embodiments, the core volume is between about 5 nm$^3$ to about 25 nm$^3$. Cores with such dimensions can be overcoated with relatively thick shells to achieve nanocrystal volumes having less than about 300 nm$^3$ (e.g., less than 250 nm$^3$; or less than 200 nm$^3$; or less than about 150 nm$^3$; or less than about 100 nm$^3$ or less than about 50 nm$^3$). Certain core-shell nanocrystals described herein have a volume of about 100 nm$^3$ to about 350 nm$^3$; or about 100 nm$^3$ to about 150 nm$^3$; or about 150 nm$^3$ to about 200 nm$^3$;

or about 200 nm$^3$ to about 250 nm$^3$; or about 250 nm$^3$ to about 300 nm$^3$; or about 300 nm$^3$ to about 350 nm$^3$.

Core-shell nanocrystals with overall volumes as described above can be prepared by overcoating relatively small cores (e.g., 1-10 nm) with multiple monolayers of shell material, as described herein. Overcoating of cores with multiple shell monolayers can produce core/shell particles having an overall volume of greater than about 50 nm$^3$; or greater than about 100 nm$^3$; or greater than about 150 nm$^3$; or greater than about 200 nm$^3$. In certain embodiments, a relatively small core (e.g., 2-4 nm diameter) can be overcoated with a relatively thick shell to produce a nanocrystal having an overall volume of about 100 nm$^3$ to about 270 nm$^3$. The aforementioned core/shell combinations are provided merely for illustrative purposes and many other combinations can produce the volume ratios described herein.

In certain embodiments, a core having a volume of between about 5 nm$^3$ to about 30 nm$^3$ is overcoated with a shell having sufficient thickness to produce a core/shell nanocrystal having an overall volume of greater than about 80 nm$^3$ (e.g., about 80 nm$^3$ to about 400 nm$^3$) such that the shell:core volume ratio is between about 10:1 and 95:1. In certain embodiments, a core having a volume of between about 5 nm$^3$ to about 30 nm$^3$ is overcoated with a shell having sufficient thickness to produce a core/shell nanocrystal having a volume of greater than about 100 nm$^3$ (e.g., about 100 nm$^3$ to about 350 nm$^3$) such that the shell:core volume ratio is between about 10:1 and 80:1. In certain embodiments, a core having a volume of between about 5 nm$^3$ to about 30 nm$^3$ is overcoated with a shell having sufficient thickness to produce a core/shell nanocrystal having a volume of greater than about 150 nm$^3$ (e.g., about 150 nm$^3$ to about 300 nm$^3$) such that the shell:core volume ratio is between about 10:1 and 30:1. In certain embodiments, a core having a volume of between about 5 nm$^3$ to about 20 nm$^3$ is overcoated with a shell having sufficient thickness to produce a core/shell nanocrystal having a volume of between about 100 nm$^3$ to about 270 nm$^3$, such that the shell:core volume ratio is between about 10:1 and 25:1.

Nanocrystals having such dimensions can be constructed to emit across the visible spectral range, and often at wavelengths of 620 nm or less; or less than 610 nm; or less than 600 nm; or less than 590 nm; or less than 580 nm; or less than 560 nm; or less than 540 nm. Further, these materials can emit at these relatively short wavelengths while still exhibiting extremely high extinction coefficients (e.g, greater than about 3,000,000 cm$^{-1}$M$^{-1}$; or greater than about c; or greater than about 10,000,000 c cm$^{-1}$M$^{-1}$; or greater than about 15,000,000 cm$^{-1}$M$^{-1}$ when excited at a wavelength of 405 nm). For example, certain populations of core/shell nanocrystals disclosed herein have shell:core volume ratios of between about 10:1 to about 30:1, emit at a maximum wavelength of about 570 nm to about 620 nm. These populations are relatively monodisperse, as evidenced by maximum emission linewidths of about 20 to about 40 nm FWHM. Further, these nanocrystal populations are extremely bright and have high extinction coefficients ranging from about 4,000,000 cm$^{-1}$M$^{-1}$ to about 15,000,000 cm$^{-1}$M$^{-1}$ and high quantum yields (QY) when measured in organic or aqueous medium (e.g., greater than about 40%, or greater than 60%; or greater than 80%; or greater than 85%).

The relative amount of shell material relative to core material for a nanocrystal also can be described using a ratio of the cross-sectional area of the nanocrystal (which includes the contribution of the core and the shell) to the cross-sectional area of the core ($A_{core+shell}/A_{core}$), where the cross-sectional areas can be measured using standard imaging techniques, such as TEM. This approach may be advantageous where volume ratios are not readily available.

The relative amount of shell material relative to core material for a nanocrystal as described herein also can be ascertained by comparing certain features in the absorbance spectrum. It is well known that different semiconductor core and shell materials absorb light preferentially at different wavelengths. Thus, a convenient measure of the amount of core and shell material present in a core-shell nanocrystal can be obtained by calculating a ratio of absorbance intensities at specific wavelengths indicative of core and shell materials from an absorbance spectrum of the core-shell nanocrystal. For certain nanocrystals provided herein, it can be convenient to compare the absorbance intensity at an excitation wavelength of 405 nm (i.e., the wavelength of a commonly used laser), which is dominated by the shell material, relative to the intensity of the band-edge absorbance, which is dominated by the core material.

Thus, in one aspect, a ratio of absorbance intensity measured at an excitation wavelength of 405 nm to the band edge absorbance ($A_{405\ nm}/A_{band-edge}$) can be calculated to provide information about the relative thickness of the shell for a core-shell nanocrystal. In general, a higher $A_{405\ nm}/A_{band-edge}$ ratio is indicative of a thicker shell. The ratio of the absorbance intensity of the population measured at an excitation wavelength of 405 nm to the absorbance intensity measured at the band edge absorbance wavelength ($A_{405\ nm}/A_{band-edge}$) for the nanocrystals described herein is typically greater than about 6 but less than about 100. For example, nanocrystals are provided herein with $A_{405\ nm}/A_{band-edge}$ of about 6 to about 80; or about 6 to about 60; or about 6 to about 40; or about 6 to about 30; or about 6 to about 20; or any value between these ranges.

For certain types of nanocrystals, the band-edge absorbance is not well-defined. In these cases, it can be more convenient to estimate the band-edge absorbance. An estimate of band-edge absorbance can be determined based on the emission wavelength maximum ($\lambda_{em}$) of the core-shell nanocrystal. Typically, there is a modest wavelength shift between the maximum emission wavelength and the band-edge absorbance for a core-shell nanocrystal. For example, typical CdSe/ZnS nanocrystals that emit in the visible range exhibit a shift between maximum emission wavelength relative to the band-edge absorbance that is typically less than about 25 nm. An estimated band-edge absorbance value can be measured at a wavelength calculated by subtracting 25 nm from the maximum emission wavelength of the core-shell nanocrystal ($A_{(\lambda em-25\ nm)}$). A ratio of $A_{405\ nm}/A_{(\lambda em-25\ nm)}$ can provide information about the relative thickness of the shell for a core-shell nanocrystal. In general, a higher $A_{405\ nm}/A_{(\lambda em-25\ nm)}$ ratio is indicative of a thicker shell. The nanocrystals provided herein typically have a $A_{405\ nm}/A_{(\lambda em-25\ nm)}$ ratio of greater than about 6 but less than about 150. In certain embodiments, the $A_{405\ nm}/A_{(\lambda em-25\ nm)}$ ratio is greater than 8; or greater than 10; or greater than 20; or greater than 30; or greater than 40; or greater than 50; or greater than about 100; or greater than about 125; or any value between these.

The disclosed nanocrystal(s) can further include a surface coating in direct contact with the external shell that can impart certain physical/chemical characteristics to the nanocrystal(s), protect the nanocrystal(s) from degradation, and/or allow the nanocrystal(s) to bind to biomolecules. In some embodiments, the disclosed nanocrystal(s) have surface coatings (in direct contact with the external layer) adding various functionalities that facilitate the nanocrystals being water-dispersable or soluble in aqueous solutions.

There are a number of suitable surface organic coatings (e.g., small hydrophilic ligands) that can be applied to the disclosed nanocrystals. Typically, these coating materials include a group(s) for attachment to the nanocrystal surface and a hydrophilic group(s), such as carboxylic acids, hydroxyls, amines, and the like. A number of suitable surface coatings can be employed to permit aqueous dispersibility of the described nanocrystals, including, but not limited to, amphiphilic polymer (AMP), lipids, phospholipids, fatty acids, polynucleic acids, and polyethylene glycol (PEG). Other coating materials include thiol containing compounds (e.g., mercapto caroboxylic acids, such as MUA), bidentate thiols (i.e., DHLA), tridentate thiols, oligopeptides (e.g., dipeptides), amine or carboxylic acid containing organic molecules (e.g., HDA), functionalized organophosphorous compounds (e.g., phosphonic acids, phosphinic acids), hydrophilic phosphonic acids, or hydrophilic oligimers having phosphonate, phosphinate, amine, carboxylate, thiol, imidizole, phosphine, nitrile, or isonitrile functionality. In certain embodiments, an inorganic (non-semiconductor) shell layer, such as zirconia, titania, silica, ZnS, ZnO, or MgO, can be applied over the semiconductor shell to impart beneficial surface properties to the nanocrystal. Various ligands and coating materials also are described in, e.g., U.S. Pat. Nos. 6,048,616, 5,990,479, 5,690,807, 5,505,928 and 5,262,357, as well as International Patent Publication No. WO 99/26299 and co-pending PCT Application Serial No. PCT/US09/59117; PCT/US09/59409; PCT/US09/53018; PCT/US09/59456; PCT/US09/61941; and PCT/US09/61953, the contents of which are expressly incorporated herein by reference in their entirety.

For certain applications, it may be desirable to attach an affinity molecule to the nanocrystal surface. For example, the nanocrystal can include a surface coating capable of linking to an affinity molecule, such as a biological molecule. Biological affinity molecules include, for example, nucleic acids, oligonucleotides, nucleotides, proteins, antibodies, peptides, carbohydrates, and the like). Thus, in another aspect, a nanocrystal or population of thereof further includes a plurality of linking agents capable of linking the nanocrystals to affinity molecules. In some embodiments, a nanocrystal may be conjugated to a molecule or species for detection by means of FRET. Examples of conjugates include, but are not limited to, dipeptide, dipeptide-BSA, dipeptide-BSA-biotin, dipeptide-BSA-streptavidin, dipeptide-BSA-biotin-polymerase, and dipeptide-BSA-HIS-polymerase conjugates. In a specific embodiment, the conjugate comprises Klenow (1×, 5×, & 15× polymerases per nanocrystal). In another specific embodiment, the conjugate can comprise phi-29 (1×, 5×, and 15× polymerases per nanocrystal). For example, nanocrystals coated with DHLA can be conjugated to a His6-modified polymerase, with optional inclusion of coating proteins such as BSA or inert His6-modified proteins.

Also provided herein are compositions that include a nanocrystal or a population thereof, as described herein. Such compositions can be aqueous or organic dispersions (e.g., colloidal dispersions) of nanocrystals in an aqueous (e.g., water or buffer) or an organic medium (e.g., an organic solvent or a polymer). In certain embodiments, the nanocrystals are provided in polymeric medium or matrix; or in a carrier, where the composition is suitable for use as a fluorescent ink; or as part of a photovoltaic or light-emitting device. In other embodiments, a composition is provided that includes nanocrystals associated with a substrate. In some embodiments, the nanocrystals are embedded in a polymeric matrix or film. Such constructs can be used in various applications, such as, for example, a component in a solar cell or panel.

The nanocrystals and compositions described herein also can form part of a kit. Kits for various biological applications are provided herein (e.g., cellular labeling). Thus, in another aspect is provided a kit for labeling cells with a population of nanocrystals, comprising: an aqueous dispersion of nanocrystals; and optionally instructions for labeling cells with the population of nanocrystals.

Also disclosed herein are methods of making a bright, photostable and PRET efficient nanocrystal and populations thereof with high extinction coefficients and modulated, reduced or no fluorescence intermittency or "blinking". These nanocrystals can include a relatively thick shell prepared by a sequential shell material deposition process, whereby one shell material is added at a time, to provide a nanocrystal having a shell of desired thickness that is substantially free of defects.

The methods described herein are capable of overcoming various problems associated with the production of bright, small semiconductor nanocrystals, including lattice mismatch between core and shell materials and Ostwald ripening. These lattice-matched shell materials can effectively reduce leakage of excitons into the shell, while minimizing red-shifting of the emission band of the core-shell nanocrystal, even if relatively thick shells are applied (e.g., greater than 5 monolayers).

The methods provided herein also provide a means for tuning nanocrystal brightness without compromising other favorable optical properties (e.g., photostability, color purity or suppressed intermittent blinking). The brightness of the nanocrystal can be tuned by adjusting the composition and/or thickness of the semiconductor shell. The methods can be implemented using any type of semiconductor core; however, certain unique optical properties are achieved when relative small cores are used in conjunction with relatively thick shells (e.g., high extinction coefficients). The nanocrystals prepared by the methods described herein comprise a shell that is substantially uniform in coverage around the core and is substantially free of defects. Shell quality can be discerned from the quantum yield of the nanocrystals. Thus, provided herein are high quality nanocrystals with quantum yield of greater than about 40%, preferably greater than about 50%, when measured at room temperature in either an organic or aqueous medium.

The nanocrystals can be synthesized to the desired size by sequential, controlled addition of two or more semiconductor materials to build and/or apply monolayers of shell material to the core. The shell growth methods described herein can be implemented using any type of nanocrystal core described herein. The present methods differ from conventional methods of adding shells where materials (e.g., diethylzinc and bis(trimethylsilyl)sulfide) are added concurrently during the synthesis. Further, sequential addition permits the formation of relatively thick (e.g., >2 nm), uniform shells (e.g., uniform size and depth) on a core. Appropriate amounts of the shell precursors are added to form a single monolayer to each nanocrystal core. The amount of shell precursors that need to be added for each monolayer addition is based on the starting size of the underlying core. Since the underlying core size typically increases over the course of the reaction, a new "core" size needs to be determined with each addition by taking the previous "core" volume and adding to it the thickness of just-added shell monolayer.

Each monolayer of shell material can be independently selected, and may be made up of a single component, or may comprise a multi-component (e.g., alloyed) shell material. In some embodiments, it is suitable to apply one or more sequential monolayers of a first shell material, followed by one or more sequential monolayers of a second shell material. This approach allows the deposition of at least one inner shell layer of a material having a bandgap and lattice size compatible with the core, followed by the deposition of at least one outer shell layer of a material having a bandgap and lattice size compatible with the inner shell layer. In some embodiments, multiple sequential monolayers of a single shell material can be applied to provide a uniform shell of a desired number of monolayers of a single shell material; in these embodiments, the first and second shell materials are the same. In other embodiments, sequential monolayers of an alloyed shell material are applied, where the ratio of the components varies such that the composition becomes successively enriched in one component of the multi-component mixture as the successive monolayers of shell material are deposited. Various shell deposition methods are described in, for example, PCT/US09/61951 and PCT/US09/61953, the contents of which are incorporated herein by reference in their entirety.

Thus, in one aspect is provided a method for making a nanocrystal that comprises a core and a layered shell, wherein the shell can comprise at least one inner shell layer and at least one outer shell layer. The method includes providing a mixture comprising a core and at least one coordinating solvent; adding a first inner shell precursor alternately with a second inner shell precursor in layer additions, to form an inner shell layer that is a desired number of layers thick; and adding a first outer shell precursor alternately with a second outer shell precursor in layer additions, to form an outer shell layer that is a desired number of layers thick. If the coordinating solvent of is not amine, the method further can include an amine. The reaction mixture can be heated to a temperature that is suitable for shell formation before and/or after every sequential addition of a shell precursor.

One representative construction can include a CdS—ZnS shell on a CdSe core. The shells for these materials can have varying numbers of layers of CdS and ZnS. Exemplary materials containing a CdSe core and multiple monolayers of CdS and multiple monolayers of ZnS were prepared as described in the examples provided herein.

Methods are also provided for making a nanocrystal that includes a core and a layered gradient shell, wherein the shell includes a multi-component (e.g., alloy, etc.) shell material of the form $M^1_xM^2_yX$, where x and y represent the ratio of $M^1$ and $M^2$ in the shell material. This method can include: (a) providing a mixture including a core, at least one coordinating solvent; (b) heating the mixture to a temperature suitable for formation of the shell layer; and (c) adding a first inner shell precursor comprising $M^1_x$ and $M^2_y$, alternately with a second inner shell precursor including X in layer additions, wherein the ratio of y to x gradually increases in sequential layer additions, such that the shell layers becomes successively enriched in $M^2$, to form a layered gradient shell that is a desired number of monolayers thick. If the coordinating solvent is not an amine, at least one amine can be included in step (a).

A representative method produces a nanocrystal having a layered gradient shell, wherein the core includes CdSe and the shell includes sequential layers of $Cd_xZn_yS$, where the ratio of y to x increases gradually from the innermost shell layer to the outermost shell layer, to provide a layered gradient shell with a finely graded potential. In some such embodiments, the outermost shell layer is essentially pure ZnS. In some embodiments, the percent of Zn in the gradient shell varies from less than about 10% at the innermost shell layer to greater than about 80% at the outermost shell layer.

Methods are provided herein to prepare nanocrystals or populations thereof that include a semiconductor core and an alloyed shell. Nanocrystals including alloyed shells of the requisite thickness can be produced using any number of conventional procedures. Alternative methods provided herein allow for fine and controlled addition of semiconductor shell precursors to induce self-assembly of an alloy during the shell growth reaction. A "self-assembled alloy," as used herein, refers to an alloy, such as an alloy of semiconductor materials, in which the components spontaneously assemble until a stable, ordered structure of minimum energy is reached. Self-assembled alloys can be formed when two or more semiconductor precursors having similar reactivity are simultaneously present in a nanocrystal growth solution (e.g., a solution containing a plurality of nanocrystal cores). Semiconductor precursors typically find their appropriate location, e.g., by diffusing through a solution, based on their physical and chemical properties. Generally, a self-assembled alloy can be formed when the semiconductor precursor(s) is added to the solution in excess relative to the amount of nanocrystals. One method for preparing a self-assembled alloy involves applying sequential monolayers of shell material to the nanocrystal cores, where the ratio of the semiconductor precursors is varied over the course of monolayer deposition. As the successive monolayers of shell material are deposited, the shell composition becomes successively enriched in one component. Once the desired number of monolayers has been deposited, the shell precursors can self-assemble to form an alloy. Since the precursor(s) are used in excess relative to the growing nanocrystals, these precursors remain unreacted in the reaction mixture upon addition of further precursor materials. This is in contrast to methods wherein a stoichiometric or near-stoichiometric amount of semiconductor precursors are added to a reaction mixture containing nanocrystals and fully or nearly-fully reacted prior to adding further precursor materials.

In one method, successive additions of a solution of shell precursors (e.g., cadmium, sulfur, selenium and/or zinc precursors) are added to semiconductor cores (e.g., CdSe) to form a relatively thick, homogeneous alloyed shell on the cores. In another method, constant concentrations of different shell precursors are added to a solution of cores in an alternating manner. For example, solutions of shell precursors can be added one at a time in an alternating manner and then allowed to react (i.e., self-assemble) for a given time period to form an alloyed shell. In yet another method, a first solution of shell precursor (e.g., cadmium precursor) can be added to a solution of cores in an alternating manner with a solution containing a second shell precursor or a mixture of two or more shell precursors (e.g., sulfur and zinc precursors). Upon addition of the first and second precursor solutions, an alloyed shell can self-assemble on the nanocrystal. Successive, alternating additions of shell precursors can be applied to the nanocrystal to build up the desired thickness of shell material.

Thus, in one aspect, a method of making a nanocrystal or population thereof is provided. The nanocrystal can include a core and a self-assembled alloyed shell. The method can include a) providing a first mixture including a plurality of semiconductor nanocrystal cores and at least one coordinating solvent; b) adding to the first mixture a first semiconductor shell precursor and a second semiconductor shell precursor; wherein the first and second semiconductor shell precursors are different; c) heating the reaction mixture during addition of the first and second shell precursors for a period of time sufficient to induce formation of a semiconductor shell layer on the core. The first semiconductor shell precursor can be added to the first mixture alternately with a second mixture, the second mixture comprising a combination of two or more shell precursors, wherein each of the semiconductor shell precursors are different. In certain embodiments, an additional shell precursor is added to the first mixture prior to alternately adding the first semiconductor shell precursor and the second mixture. The additive can include an element used in the semiconductor core. For example, where a CdSe core is used, the core can first be treated with a cadmium precursor prior to treatment with the first and/or second shell precursor(s). Alternatively, the additive can be included with the first and/or second mixtures.

In certain embodiments, the nanocrystal includes a semiconductor alloy shell layer formed of an alloy or mixture of Cd, S, Se, and/or Zn. For example, shells can be formed of ZnS, CdS, CdZnS, CdSeZn, ZnSeS, or CdSeZnS. In some embodiments, an alloyed shell can include metal atoms selected from Cd, Zn, Ga and Mg. The second element in these semiconductor shell layers is frequently selected from S, Se, Te, P, As, N and Sb. Certain methods provided herein produce nanocrystals with relatively thick, alloyed ZnSSe shells. The alloyed shell can be formed in such a manner as to produce a compositional gradient between core and shell of one or shell materials. For example, depending on the order of shell precursor addition and the time and temperature used during the shelling reaction, a shell can be produced with a concentration of Cd that is higher near the core and lower near the surface. Methods are provided herein to produce nanocrystals with relatively thick, alloyed CdZnS shells, where the concentration of Cd forms a more or less smooth compositional gradient between these extremes as the distance from the semiconductive core increases.

The nanocrystals produced by the methods provided herein can include a plurality of shell monolayers. The monolayers may not always be completely distinct as they may, in some embodiments, be a latticing between the surfaces of contacting monolayers. In some embodiments, a layered shell can be about 3-20 monolayers of shell material thick, but typically 19 monolayers or less, as described herein. In some embodiments having an inner shell and an outer shell, at least one inner shell layer can be comprised of about 3-5 monolayers, sometimes about 3-7 monolayers, of the first shell material. In other embodiments, at least one outer shell layer can be comprised of about 3-5 monolayers, sometimes about 3-7 monolayers, of the second shell material. In some embodiments, the inner shell layer can be at least 3 monolayers thick; in other embodiments, the outer shell layer can be at least 3 monolayers thick.

In further embodiments, for either the inner or outer layer, or both, less than a full layer of the appropriate first shell precursor can be added alternately with less than a full layer of the appropriate second shell precursor, so the total amount of the first and second shell precursor required is added in two or more portions. Sometimes, the portion is about 0.25 monolayers of shell material, so that the 4 portions of 0.25 monolayer of first shell precursor are added alternately with 4 portions of 0.25 monolayer of second shell precursor; sometimes the portion is about 0.5 monolayers of shell material, and sometimes about 0.75 monolayers of shell material.

Precursors useful as the "first" precursor in the methods provided herein include compounds containing elements from Groups 2 and 12 of the Periodic Table of the Elements (e.g., Zn, Cd, Hg, Mg, Ca, Sr, Ba, and the like), compounds containing elements from Group 13 of the Periodic Table of the Elements (Al, Ga, In, and the like), and compounds containing elements from Group 14 of the Periodic Table of the Elements (Si, Ge, Pb, and the like). Many forms of the precursors can be used in the disclosed methods.

Examples of compounds useful as the first precursor can include, but are not limited to: organometallic compounds such as alkyl metal species, salts such as metal halides, metal acetates, metal carboxylates, metal phosphonates, metal phosphinates, metal oxides, or other salts. In some embodiments, the first precursor provides a neutral species in solution. For example, alkyl metal species such as diethylzinc ($Et_2Zn$) or dimethyl cadmium are typically considered to be a source of neutral zinc atoms)($Zn^0$) in solution. In other embodiments, the first precursor provides an ionic species (i.e., a metal cation) in solution. For example, zinc chloride ($ZnCl_2$) and other zinc halides, zinc acetate ($Zn(OAc)_2$) and zinc carboxylates are typically considered to be sources of $Zn^{2+}$ cations in solution.

By way of example only, suitable first precursors providing neutral metal species include dialkyl metal sources, such as dimethyl cadmium ($Me_2Cd$), diethyl zinc ($Et_2Zn$), and the like. Suitable first precursors providing metal cations in solution include, e.g., cadmium salts, such as cadmium acetate ($Cd(OAc)_2$), cadmium nitrate ($Cd(NO_3)_2$), cadmium oxide (CdO), and other cadmium salts; and zinc salts such as zinc chloride ($ZnCl_2$), zinc acetate ($Zn(OAc)_2$), zinc oleate ($Zn(oleate)_2$), zinc chloro(oleate), zinc undecylenate, zinc salicylate, and other zinc salts. In some embodiments, the first precursor is salt of Cd or Zn. In some embodiments, it is a halide, acetate, carboxylate, or oxide salt of Cd or Zn. In other embodiments, the first precursor is a salt of the form $M(O_2CR)X$, wherein M is Cd or Zn; X is a halide or $O_2CR$; and R is a C4-C24 alkyl group that is optionally unsaturated. Other suitable forms of Groups 2, 12, 13 and 14 elements useful as first precursors are known in the art.

Precursors useful as the "second" precursor in the disclosed methods include compounds containing elements from Group 16 of the Periodic Table of the Elements (e.g., S, Se, Te, and the like), compounds containing elements from Group 15 of the Periodic Table of the Elements (N, P, As, Sb, and the like), and compounds containing elements from Group 14 of the Periodic Table of the Elements (Ge, Si, and the like). Many forms of the precursors can be used in the disclosed methods. It will be understood that in some embodiments, the second precursor will provide a neutral species in solution, while in other embodiments the second precursor will provide an ionic species in solution.

When the first precursor comprises a metal cation, the second precursor can provide an uncharged (i.e., neutral) non-metal atom in solution. In frequent embodiments, when the first precursor comprises a metal cation, the second precursor contributes a neutral chalcogen atom, most commonly $S^0$, $Se^0$ or $Te^0$.

Suitable second precursors for providing a neutral chalcogen atom include, for example, elemental sulfur (often as a solution in an amine, e.g., decylamine, oleylamine, or dioctylamine, or an alkene, such as octadecene), and trialkylphosphine adducts of S, Se and Te. Such trialkylphosphine adducts are sometimes described herein as $R_3P=X$, wherein X is S, Se or Te, and each R is independently H, or a $C_1$-$C_{24}$ hydrocarbon group that can be straight-chain, branched, cyclic, or a combination of these, and which can be unsaturated. Exemplary second precursors of this type include tri-n (butylphosphine)selenide (TBP=Se), tri-n-(octylphosphine)selenide (TOP=Se), and the corresponding sulfur and tellurium reagents, TBP=S, TOP=S, TBP=Te and TOP=Te. These reagents are frequently formed by combining a desired element, such as Se, S, or Te with an appropriate coordinating solvent, e.g., TOP or TBP. Precursors that provide anionic species under the reaction conditions are typically used with a first precursor that provides a neutral metal atom, such as alkylmetal compounds and others described above or known in the art.

In some embodiments, the second precursor provides a negatively charged non-metal ion in solution (e.g., $S^{-2}$, $Se^{-2}$ or $Te^{-2}$). Examples of suitable second precursors providing an ionic species include silyl compounds such as bis(trimethylsilyl)selenide (($TMS)_2Se$), bis(trimethylsilyl)sulfide (($TMS)_2S$) and bis(trimethylsilyl)telluride (($TMS)_2Te$). Also included are hydrogenated compounds such as $H_2Se$, $H_2S$, $H_2Te$; and metal salts such as NaHSe, NaSH or NaHTe. In this situation, an oxidant can be used to oxidize a neutral metal species to a cationic species that can react with the anionic precursor in a 'matched' reaction, or an oxidant can be used increase the oxidation state of the anionic precursor to provide a neutral species that can undergo a 'matched' reaction with a neutral metal species.

Other exemplary organic precursors are described in U.S. Pat. Nos. 6,207,299 and 6,322,901 to Bawendi et al., and synthesis methods using weak acids as precursor materials are disclosed by Qu et al., (2001), Nano Lett., 1(6):333-337, the disclosures of each of which are incorporated herein by reference in their entirety.

In certain embodiments, the first and second semiconductor shell precursor comprise a Group 12 element, e.g., Cd or Zn. In other embodiments, three or more shell precursors are used. For example, the first and second semiconductor shell precursor comprise a Group 12 element, e.g., Cd or Zn, and the third semiconductor shell precursor comprises a Group 16 element (e.g., S, Se, O, Te, a halogen (e.g., F), or a pnictide (e.g., N, P, As, Sb).

Both the first and the second precursors can be combined with an appropriate solvent (e.g., alkyl phosphines, alkyl phosphine oxides, alkyl phosphonic acids, alkyl phosphinic acids, or carboxylic acid containing solvents, or mixtures of these) to form a solution for use in the disclosed methods. The solvent or solvent mixture used to form a first precursor solution may be the same or different from that used to form a second precursor solution.

Shell precursors can be represented as a M-source and an X-donor. The M-source can be an M-containing salt, such as a halide, carboxylate, phosphonate, carbonate, hydroxide, or diketonate, or a mixed salt thereof (e.g., a halo carboxylate salt, such as Cd(halo)(oleate)), of a metal, M, in which M can be, e.g., Cd, Zn, Mg, Hg, Al, Ga, In, or Tl. In the X-donor, X can be, e.g., O, S, Se, Te, N, P, As, or Sb. The mixture can include an amine, such as a primary amine (e.g., a $C_8$-$C_{20}$ alkyl amine). The X donor can include, for example, a phosphine chalcogenide, a bis(trialkylsilyl)chalcogenide, a dioxygen species, an ammonium salt, or a tris(trialkylsilyl)phosphine, or the like.

The M-source and the X donor can be combined by contacting a metal, M, or an M-containing salt, and a reducing agent to form an M-containing precursor. The reducing agent can include an alkyl phosphine, a 1,2-diol or an aldehyde, such as a $C_6$-$C_{20}$ alkyl diol or a $C_6$-$C_{20}$ aldehyde.

Alkyl typically refers to a branched or unbranched saturated hydrocarbon group of 1 to 100 carbon atoms, preferably 1 to 30 carbon atoms, such as methyl, ethyl, n-propyl, isopropyl, n-butyl, isobutyl, t-butyl, octyl, decyl, tetradecyl, hexadecyl, eicosyl, tetracosyl and the like, as well as cycloalkyl groups such as cyclopentyl, cyclohexyl and the like. Optionally, an alkyl can contain 1 to 6 linkages selected from the group consisting of —O—, —S—, -M- and —NR— where R is hydrogen, or $C_1$-$C_8$ alkyl or lower alkenyl.

Suitable M-containing salts include, for example, cadmium acetylacetonate, cadmium iodide, cadmium bromide, cadmium chloride, cadmium hydroxide, cadmium carbonate, cadmium acetate, cadmium oxide, zinc acetylacetonate, zinc iodide, zinc bromide, zinc chloride, zinc hydroxide, zinc carbonate, zinc acetate, zinc oxide, magnesium acetylacetonate, magnesium iodide, magnesium bromide, magnesium chloride, magnesium hydroxide, magnesium carbonate, magnesium acetate, magnesium oxide, mercury acetylacetonate, mercury iodide, mercury bromide, mercury chloride, mercury hydroxide, mercury carbonate, mercury acetate, aluminum acetylacetonate, aluminum iodide, aluminum bromide, aluminum chloride, aluminum hydroxide, aluminum carbonate, aluminum acetate, gallium acetylacetonate, gallium iodide, gallium bromide, gallium chloride, gallium hydroxide, gallium carbonate, gallium acetate, indium acetylacetonate, indium iodide, indium bromide, indium chloride, indium hydroxide, indium carbonate, indium acetate, thallium acetylacetonate, thallium iodide, thallium bromide, thallium chloride, thallium hydroxide, thallium carbonate, or thallium acetate. Suitable M-containing salts also include, for example, carboxylate salts, such as oleate, stearate, myristate, and palmitate salts, mixed halo carboxylate salts, such as M(halo)(oleate) salts, as well as phosphonate salts.

The X donor is a compound capable of reacting with the M-containing salt to form a material with the general formula MX. The X donor is generally a chalcogenide donor or a phosphine donor, such as a phosphine chalcogenide, a bis(silyl) chalcogenide, dioxygen, an ammonium salt, or a tris(trialkylsilyl) phosphine. Suitable X donors include dioxygen, elemental sulfur, bis(trimethylsilyl) selenide (($TMS)_2Se$), trialkyl phosphine selenides such as (tri-n-octylphosphine) selenide (TOPSe) or (tri-n-butylphosphine) selenide (TBPSe), trialkyl phosphine tellurides such as (tri-n-octylphosphine) telluride (TOPTe) or hexapropylphosphorustriamide telluride (HPPTTe), bis(trimethylsilyl) telluride (($TMS)_2Te$), sulfur, bis(trimethylsilyl)sulfide (($TMS)_2S$), a trialkyl phosphine sulfide such as (tri-n-octylphosphine) sulfide (TOPS), tris(dimethylamino) arsine, an ammonium salt such as an ammonium halide (e.g., $NH_4Cl$), tris(trimethylsilyl) phosphide (($TMS)_3P$), tris(trimethylsilyl) arsenide (($TMS)_3As$), or tris(trimethylsilyl) antimonide (($TMS)_3Sb$). In certain embodiments, the M donor and the X donor can be moieties within the same molecule.

In some embodiments, mismatched precursors can be chosen such that one precursor provides a neutral atom in solution under the reaction conditions, while the other precursor provides an ion. For example, a mixture of cadmium alkylphosphonate, which is a source of $Cd^{2+}$ ions, and trioctylphosphine selenide (TOPSe), which is a source of $Se^0$, might be employed as mismatched precursors. Such precursors cannot react to form a neutral species unless an electron transfer agent is present to adjust the oxidation state of one of the reactive species to provide 'matched' species capable of undergoing reaction. For example, a reductant could be used to add electrons to $Cd^{2+}$ to provide two non-ionic species (i.e., $Cd^0$ and $Se^0$), or it could add electrons to $Se^0$ to provide two ionic species (i.e., $Cd^{2+}$ and Se$^{2-}$). Either way, once the atomic species are 'matched', their reaction can proceed, but the reaction cannot proceed without such an electron transfer agent. Alternatively, two ionic species having the same charge (i.e., two cations or two anions) would also be considered to be 'mismatched.' For example, mismatched precursors that provide two cationic species could be used, where one species is reduced to provide an anionic species capable of undergoing a 'matched' reaction. For example, Se$^{2+}$ or Se$^{4+}$ could be reduced to provide selenide anion Se$^{2-}$, which could undergo reaction with a metal cation species, such as Cd$^{2+}$. In another example, two cationic species could both be reduced to neutral species.

The reaction mixture can be heated for a time sufficient to deposit about multiple monolayers of shell material on the core. The temperature is selected to optimize controlled deposition of precursor materials on the surface of the growing nanocrystal and to minimize lattice mismatch and other defects. Typically, the heating steps in the disclosed methods are conducted at a temperature within the range of about 150-350° C., more preferably within the range of about 200-300° C. In some embodiments, the temperature suitable for formation of at least one inner shell layer is about 215° C. In some embodiments, the temperature suitable for formation of at least one outer shell layer is about 245° C. It is understood that the above ranges are merely exemplary and are not intended to be limiting in any manner as the actual temperature ranges may vary, dependent upon the relative stability of the precursors, ligands, and solvents. Higher or lower temperatures may be appropriate for a particular reaction. The determination of suitable time and temperature conditions for providing nanocrystals is within the level of skill in the art using routine experimentation.

The temperature can be chosen to minimize the Ostwald ripening process. As discussed above, Ostwald ripening is a common phenomenon and is especially pronounced for the production of small nanocrystals under standard high temperature synthesis methods typically used during the nanocrystal shell growth process. It has been found that in certain methods Ostwald ripening can be minimized by adding shell precursors to a solution of cores at a lower temperature (e.g., 100° C. or below) and then increasing the temperature over time (e.g., to temperatures of 200° C. or greater). The temperature can be increased in a step-wise fashion or ramped up gradually in a linear fashion. In certain embodiments, the temperature can be increased in a relatively linear fashion from about 50° C. to about 300° C. during the course of the shelling reaction. Certain methods ramp the temperature from about 100° C. to about 215° C. Once the particles are sufficiently large, such that ripening was no longer a major issue, the temperature can be increased to the point where high-quality, defect-free shells can be grown.

It can be advantageous to conduct the nanocrystal-forming or shell-growth reactions described herein with the exclusion of oxygen and moisture. In some embodiments the reactions are conducted in an inert atmosphere, such as in a dry box. The solvents and reagents are also typically rigorously purified to remove moisture and oxygen and other impurities, and are generally handled and transferred using methods and apparatus designed to minimize exposure to moisture and/or oxygen. In addition, the mixing and heating steps can be conducted in a vessel that is evacuated and filled and/or flushed with an inert gas such as nitrogen. The filling can be periodic or the filling can occur, followed by continuous flushing for a set period of time.

The methods described herein are conducted in a solvent. The solvent can include a mixture of solvents, often referred to in the art as a "solvent system". Suitable reaction solvents include, by way of illustration and not limitation, hydrocarbons, amines, alkyl phosphines, alkyl phosphine oxides, fatty acids, carboxylic acids, ethers, furans, phosphoacids, pyridines and mixtures thereof.

In some embodiments, the solvent or solvent system can include at least one coordinating solvent. The solvent can include a coordinating solvent or a mixture of a coordinating solvent and an essentially non-coordinating solvent such as an alkane. For example, the at least one coordinating solvent can be a trialkylphosphine, a trialkylphosphine oxide, a phosphonic acid, or a mixture of these. Sometimes, the at least one coordinating solvent comprises TOP, TOPO, TDPA, EPA, OPA, or a mixture of these.

Suitable hydrocarbons include alkanes, alkenes and aromatic hydrocarbons from 10 to about 30 carbon atoms; examples include octadecene and squalane, and hydrocarbons may comprise a mixture of alkane, alkene and aromatic moieties, such as alkylbenzenes (e.g., mesitylene).

Suitable amines include, but are not limited to, monoalkylamines, dialkylamines, and trialkylamines, for example dioctylamine, oleylamine, decylamine, dodecylamine, hexyldecylamine, and so forth. Alkyl groups for these amines typically contain about 6-24 carbon atoms per alkyl, and can include an unsaturated carbon-carbon bond, and each amine typically has a total number of carbon atoms in all of its alkyl groups combined of about 10-30 carbon atoms.

Exemplary alkyl phosphines include, but are not limited to, the trialkyl phosphines, tri-n-butylphosphine (TBP), tri-n-octylphosphine (TOP), and so forth. Alkyl groups for these phosphines contain about 6-24 carbon atoms per alkyl, and can contain an unsaturated carbon-carbon bond, and each phosphine has a total number of carbon atoms in all of its alkyl groups combined of about 10-30 carbon atoms.

Suitable alkyl phosphine oxides include, but are not limited to, the trialkyl phosphine oxide, tri-n-octylphosphine oxide (TOPO), and so forth. Alkyl groups for these phosphine oxides contain about 6-24 carbon atoms per alkyl, and can contain an unsaturated carbon-carbon bond, and each phosphine oxide has a total number of carbon atoms in all of its alkyl groups combined of about 10-30 carbon atoms.

Exemplary fatty acids include, but are not limited to, stearic, oleic, palmitic, myristic and lauric acids, as well as other carboxylic acids of the formula R—COOH, wherein R is a $C_6$-$C_{24}$ hydrocarbon group and can contain an unsaturated carbon-carbon bond. It will be appreciated that the rate of nanocrystal growth generally increases as the length of the fatty acid chain decreases.

Exemplary ethers and furans include, but are not limited to, tetrahydrofuran and its methylated forms, glymes, and so forth.

Suitable phosphonic and phosphinic acids include, but are not limited to hexylphosphonic acid (HPA), tetradecylphosphonic acid (TDPA), octylphosphinic acid (OPA), and ethylphosphonic acid (EPA) and are frequently used in combination with an alkyl phosphine oxide such as TOPO. Suitable phosphonic and phosphinic acids are of the formula $RPO_3H_2$ or $R_2PO_2H$, wherein each R is independently a $C_6$-$C_{24}$ hydrocarbon group and can contain an unsaturated carbon-carbon bond.

Exemplary pyridines include, but are not limited to, pyridine, alkylated pyridines, nicotinic acid, and so forth.

Suitable alkenes include, e.g., octadecene and other $C_4$-$C_{24}$ hydrocarbons that are unsaturated.

Solvents can be used alone or in combination. TOP-TOPO solvent systems are commonly utilized in the art, as are other related (e.g., butyl) systems. For example, TOP and TOPO can be used in combination to form a cadmium solution, while TOP, alone, can be used to form a selenium solution. Also preferred are solvent mixtures can include an amine, in particular a secondary amine, with a trialkylphosphine oxide, such as TOPO.

Technical grade solvents can be used, and benefits can be obtained from the existence of beneficial impurities in such solvents, e.g. TOP, TOPO or both. In one preferred embodiment, the solvent is pure. Typically, this means that the solvent contains less than about 10 vol %, and more preferably less than about 5 vol % of impurities that can function as reductants. Solvents such as TOPO at about 90% or about 97% purity and TOP at about 90% purity are particularly well suited for use in the disclosed methods, and solvents that are greater than about 99% pure are preferred.

In some embodiments, ligands are included in the reaction. Ligands are compounds that complex with a precursor and/or a nanocrystal. Ligands can help optimize controlled deposition of precursor materials on the surface of the growing nanocrystal and to minimize lattice mismatch and other defects. Suitable ligands include, by way of illustration and not limitation, phospho-acids such as ethylphosphonic acid (EPA), butylphosphonic acid (BPA), hexylphosphonic acid (HPA) and tetradecylphosphonic acid (TDPA), carboxylic acids such as isomers of octadecanoic acid, amines, amides, alcohols, ethers, alkenes, alkynes, and mixtures thereof.

In certain methods, a mixture of ligands is used in the shell-growth reaction. Ligand mixtures can include, for example, mixtures of acidic ligands. Ligands mixtures can include, for example, mixtures of oxoacids, such as phosphonic acids (e.g., ethylphosphonic acid, butylphosphonic acid, hexylphosphonic acid, or tetradecylphosphonic acid (TDPA)), phosphinic acids, carboxylic acids, sulfonic acids, and/or boronic acids. Ligand mixtures for use in the shell-growth reaction are described in, for example, commonly owned U.S. Application No. 61/427,760 ("Preparation of Nanocrystals with Mixtures of Organic Ligands"), the contents of which are expressly incorporated herein by reference in its entirety. In some cases, the ligand and the solvent can be the same.

In certain embodiments, the semiconductor cores are treated with such an additional ligand prior to conducting the shell growth reaction. For example, the cores can be treated with a amine (e.g., an alkylamine) to prepare them for overcoating with shell precursors. In some embodiments, an amine can be included in the nanocrystal shell reaction mixture.

The maximum emission wavelength of the population of nanocrystals can be monitored during the course of the reaction, and the reaction can be halted when nanocrystals achieve a certain maximum emission wavelength (where the wavelength is indicative of nanocrystal size). In certain embodiments, the reaction is halted before the population of nanocrystals exhibits a maximum fluorescence emission wavelength in the red spectral region (e.g., no greater than 620 nm). In certain embodiments, the reaction is halted when the nanocrystal volume to core volume ratio ($V_{core+shell}/V_{core}$) is greater than about 5:1, and typically greater than about 10:1, but before the nanocrystal volume to core volume ratio reaches 100:1, and typically before it reaches 95:1.

The outer surface of the nanocrystal typically includes an organic layer derived from the coordinating solvent used during the growth process. Thus, after the growth process, the nanocrystal is hydrophobic. Hydrophobic nanocrystals are readily dispersed in or dissolved in a water-immiscible solvent like hexanes, toluene, and the like, and are not readily dispersed in water.

As described above, many biological applications require that the nanocrystals be water-dispersible or soluble in aqueous solutions. Numerous approaches have been proposed to functionalize nanocrystals to render the nanocrystals dispersible in an aqueous medium and/or to introduce linking groups for attaching the nanocrystals to biological molecules. For example, the nanocrystals prepared as described herein can be further treated with a hydrophilic polymer (e.g., amphiphilic polymer), as described in U.S. Pat. No. 6,649,138 (Adams et al.), which is expressly incorporated herein by reference in its entirety. Alternatively, a ligand exchange process can be utilized to replace the hydrophobic ligands on the nanocrystals with hydrophilic ligands to cause the plurality of nanocrystals to migrate into the aqueous phase. See PCT Application Serial No. PCT/US09/59409; PCT/US09/53018; and PCT/US09/59456, which are expressly incorporated herein by reference as if set forth in full.

Due to their superior optical properties, the nanocrystals described herein are useful in a variety of fields. The exceptionally optical properties, coupled with their stability, make the disclosed nanocrystals ideally suited for biological and diagnostic applications but they also can be utilized in many other non-biological applications. Representative biological and non-biological applications include, for example, analytical and combinatorial chemistry, medical diagnostics, genetic analysis, solar energy conversion, displays, anti-counterfeiting, and single molecule spectroscopy. The spectral emission can be associated with a variety of assays, such as immunochemistry, immunocytochemistry, immunobiology, or immunofluorescence assays; DNA sequence analyses; fluorescence resonance energy transfer, flow cytometry, or fluorescence activated cell sorting assay; diagnostics in biological systems, in vivo and in vitro imaging (e.g., cellular imaging), and high-throughput screening. Further, the nanocrystals can be used in a variety of single molecule microscopy and high throughput screening applications. Such applications include but are not limited to single-molecule FRET measurements; fluorescence correlation spectroscopy; real-time single molecule interactions such as RNA/DNA or protein-ligand; real-time single molecule DNA sequencing; analyte detection in tissues, fluid samples, cells, electrophoresis and other separation systems; intracellular and extracellular protein trafficking and localization; enzyme kinetics and control; protein sequencing; single molecule PCR; as well as macromolecular structural analysis.

Thus, in yet another aspect, a method of detecting an analyte (e.g., a biological molecule, such as, for example, nucleic acid, antibody, protein, peptide, carbohydrate, and the like) in a biological sample is provided, the method comprising contacting a biological sample (e.g., cell or cellular component, tissue, protein, biological membrane, nucleic acid, and the like) with a semiconductor nanocrystal (or a population thereof) or a nanocrystal composition as described herein for a time sufficient to for the nanocrystals to bind to the analyte in the sample, if present, and detecting the fluorescence emission of the semiconductor nanocrystal.

The following examples are offered to illustrate but not to limit the embodiments described herein.

EXAMPLES

Example 1

Preparation of CdSe/6CdS-3.5ZnS and CdSe/4CdS-3.5 ZnS Core-Shell Nanocrystals CdSe cores were prepared using standard methods, as described in U.S. Pat. Nos. 6,815,064 or 7,147,712, with growth halted at 480 nm emission. These cores were precipitated and cleaned using standard methods and resuspended into hexane for use in the shell reaction.

Solutions of a suitable cadmium precursor (such as dimethylcadmium or cadmium acetate), zinc precursor (such as diethylzinc or zinc stearate), and sulfur precursor (such as elemental sulfur or trimethylsilylsulfide [$(TMS)_2S$]) were prepared in TOP in a glove box. Each solution contained a quantity of precursor sufficient to produce the desired shell thickness, as can be calculated by one of ordinary skill in the art. Each of these solutions was taken up in separate syringes and removed from the glove box.

A 1:1 (w:v) mixture of tri-n-octylphosphine oxide (TOPO) and tri-n-octylphosphine (TOP) was introduced into a flask. Tetradecylphosphonic acid (TDPA) was added to the flask in an amount suitable to fully passivate the final material, as can be calculated from the reaction scale and the expected final nanocrystal size. The contents of the flask were heated to 125° C. under vacuum and then the flask was refilled with $N_2$ and cooled. 1.8 mL of the previously prepared core/hexane solution containing 0.5 mmol cores (optical density of 42 at the band edge) was added to the reaction flask. The hexane was removed by vacuum; the flask was then refilled with $N_2$ and 1.8 mL of decylamine was added. The flask was heated to the desired synthesis temperature, typically about 200 to about 250° C. The cadmium and sulfur precursor solutions were then added alternately in layer additions, which were based upon the starting size of the underlying cores. As each layer of shell material was added, a new "core" size was determined by taking the previous "core" size and adding to it the thickness of just-added shell material. After six (6) layers of CdS shell material were added, the cadmium precursor solution was replaced with the zinc precursor solution. Zinc and sulfur solutions were then added alternately in layer additions until three (3) layers of ZnS were added. A final layer (0.5 layer) of the zinc solution was added at the end, the reaction flask was cooled, and the product was isolated by conventional methods (Sample 1). A similar method was used to prepare CdSe/4CdS-3.5ZnS core shell nanocrystals but using a core with maximum emission wavelength of 525 nm (Sample 2).

Example 2

Preparation of CdSe/8 CdZnS and CdSe/6 CdZnS Core-Shell Nanocrystals

CdSe cores (2.6 nm diameter) were prepared and processed, as described in Example 1, with growth halted at 493 nm emission. A mixture of TOPO, TOP and TDPA, and solutions of suitable cadmium, sulfur, and zinc precursors were prepared as described in Example 1, with the exception that sulfur and zinc precursors were taken upon in the same syringe. 0.9 mL (at an optical density of 33.54 at 477 nm) of the previously prepared core/hexane solution was added to the reaction flask, the hexane was removed by vacuum at elevated temperature; the flask was then refilled with $N_2$. The flask was heated to the desired synthesis temperature, typically about 150° C. to about 250° C. The shell precursor solutions were then added alternately in layer additions, as described in Example 1. After 8 layers of shell material were added, the reaction flask was cooled, and the product was isolated by conventional methods and stored in toluene. The core shell nanocrystals (7.0 nm diameter) emitted at 587 nm with a 29 nm FWHM. The shell:core volume ratio was 19.5. The core-shell nanocrystals were treated with an amphiphilic polymer coating as described in U.S. Pat. No. 6,649,138 (Adams et al.). Absolute quantum yield of the polymer coated nanocrystals (Sample 3) measured in water was 85%; extinction coefficient=13,900,000 $M^{-1}$ $cm^{-1}$ at an excitation wavelength of 405 nm and 378,300 $M^{-1}$ $cm^{-1}$ at a 562 nm excitation wavelength. A similar procedure was used to generate a population of CdSe/6 CdZnS nanocrystals using nanocrystal cores with 480 nm maximum emission wavelength (Sample 4).

Example 3

Preparation of CdSe/4 CdZnS/3 ZnS Core-Shell Nanocrystals

CdSe cores were prepared and processed as described in Example 1 using standard methods with growth halted at 515 nm emission. Solutions of suitable cadmium, sulfur, and zinc precursors were prepared as described in Example 2. A 1:1 (w:v) mixture of tri-n-octylphosphine oxide (TOPO) and tri-n-octylphosphine (TOP) was introduced into a flask. Tetradecylphosphonic acid (TDPA) was added to the flask in an amount suitable to fully passivate the final material, as can be calculated from the reaction scale and the expected final nanocrystal size. The contents of the flask were heated to 100° C. under vacuum for 10 minutes; the flask then was refilled with $N_2$. 1.03 mL (at an optical density of 34 at the band edge) of the previously prepared core/hexane solution was added to the reaction flask and the hexane was removed by vacuum at elevated temperature; the flask was then refilled with $N_2$ and 2.1 ml decylamine was added. The temperature was raised to the desired synthesis temperature, about 200° C.-225° C., during which time. The Cd and S/Zn precursor solutions were added alternately in layer additions to form a self-assembled CdZnS alloy shell. After four (4) layers of shell material were added, the temperature then was increased slightly and three (3) additional layers of ZnS shell were added by layer additions. The reaction flask then was cooled and the reaction quenched with toluene, and the product was isolated by conventional methods and stored in toluene. For optical measurements, the product was dispersed in hexane (Sample 5) at a concentration of 2.51 µM.

A similar procedure was used to generate populations of CdSe/4 CdZnS/3 ZnS (Sample 6) and CdSe/6 CdZnS/3.5 ZnS (Sample 7) nanocrystals using nanocrystal cores have a maximum emission wavelength of 490 nm.

Example 4

Preparation of Preparation of CdSe/8 ZnSeS Core-Shell Nanocrystals

Core-shell nanocrystals were prepared from nearly spherical CdSe core nanocrystals in the presence of tetradecylphosphonic acid (TDPA) and processed, as described in Example 1, with growth halted at 530 nm emission.

A solution of a suitable zinc precursor (e.g., diethylzinc) in TOP was prepared in a glove box in a quantity sufficient to produce a desired thickness of shell. Separately, a solution of a suitable selenium precursor in TOP with up to 20% molar ratio of a suitable sulfur precursor (such as trimethylsilylsulfide [(TMS)$_2$S] or elemental sulfur) was prepared in a quantity sufficient to produce a desired shell thickness. Each of these precursor solutions was taken up in separate syringes and removed from the glove box.

A 1:1 (w:v) mixture of TOPO and TOP was introduced into a flask. Hexadecylamine was added into the flask in an amount suitable to fully passivate the final material, as can be calculated from the reaction scale and the expected final nanocrystal size. The contents of the flask were heated under vacuum and then the flask was refilled with N$_2$ and cooled. 5.1 mL (at an optical density of 24.2 at bandedge 518 nm) of the core/hexane solution was added to the reaction flask, and the hexane was removed by vacuum; the flask was then refilled with nitrogen. The flask was heated to the desired synthesis temperature, typically about 150° C. to about 300° C. The two shell precursor solutions were then added alternately in layer additions, as described in Example 1. After eight (8) layers of ZnSeS were added, the reaction flask was cooled, and the product was isolated by conventional methods. Optical properties of the product (Sample 8) were measured in organic medium.

Example 5

Comparison of Blinking Properties

The blinking behavior of nanocrystals prepared as in Example 1 can be evaluated using a standard single-particle microscopy set up, under conditions of continuous irradiation with 405 nm laser with a desired input power. The particles described herein can be compared to commercially available nanocrystals prepared by conventional methods.

As discussed above, more blinking has generally been observed with increasing laser power. To explore the effect of laser power on blinking, nanocrystals were irradiated using a high intensity blue-violet laser, having an excitation wavelength of about 405 nm. The laser was tuned to control the power, and the laser power was measured before it reached the lens. Less blinking would be expected for photo-excitation using a laser having a longer wavelength as a result of the smaller absorption cross-section of the particles at longer wavelengths. In particular, for very large nanocrystals having very thick shells, more blinking would be expected at shorter wavelengths owing to the greater amount of absorbance by the shell materials at wavelengths in the blue-violet or ultraviolet range. In addition, very large nanocrystals having very thick shells would be expected to show a greater amount of photo-bleaching at decreased wavelength, due to an increase in photoexcitation at shorter wavelengths.

Analysis using the power law parameters for those particles that could be fit to a power law also can show a marked difference between the samples. The particles can be binned into three categories: low-blinkers for which no power law fit could be obtained as a result of too little blinking (which typically indicated an $\alpha_{on}$ of below about 1.1), mid-blinkers for which an $\alpha_{on}$ of below 1.3 is measured, and high-blinkers for which an $\alpha_{on}$ between 1.3 and 1.5 is measured. For conventional particles, under an excitation rate of 150,000 photons per second, the distribution of low-medium-high blinking under these criteria was 30%-50%-20%. For the nanocrystals disclosed herein, under an increased excitation rate of 300,000 absorbed photons per second, the low-medium-high distribution can be about 25%-50%-25%.

Example 6

Optical Properties of Semiconductor Nanocrystals

Figure 2:
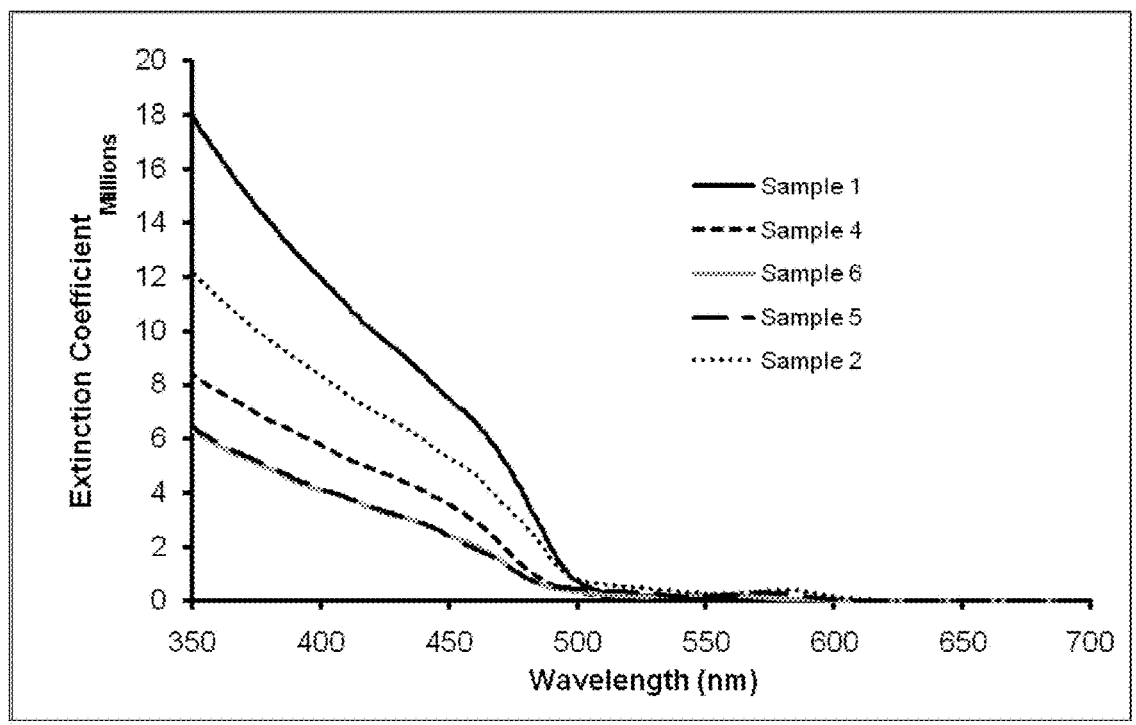
FIG. 2 is a plot of extinction coefficients for various nanocrystal preparations described herein.

The spectral properties were evaluated for the various preparations of semiconductor nanocrystals produced according to the methods described herein (Tables 1-2). Absolute quantum yield was measured on a Hammamastu Absolute PL Quantum Yield Measurement System (model number C9920-02). Quantum yields, extinction coefficients, and blinking properties ($\alpha_{on}$) were measured in toluene or hexane, unless otherwise noted. FIG. 1 and FIG. 2 show normalized absorbance spectra and extinction coefficients, respectively, for various nanocrystal preparations described herein.

TABLE 1

Emission and Blinking Properties

| Sample # | Emission Maximum (nm) | FWHM (nm) | QY | $\alpha_{on}$ |
|---|---|---|---|---|
| 1 | 579 | 38 | 0.49 | not measured |
| 2 | 599 | 29 | 0.88 | not measured |
| 3 | 587 | 29 | 0.85 | not measured |
| 4 | 571 | 31 | 0.48 | not measured |
| 5 | 591 | 28 | 0.65 | not measured |
| 6 | 571 | 29 | 0.61 | 1.37 |
| 7 | 571 | 32 | 0.37 | 1.41 |
| 8 | 520 | 28 | 0.23 | not measured |

TABLE 2

Extinction Coefficients ($M^{-1}cm^{-1}$ × millions)

| Sample # | Band Edge | 532 nm | 488 nm | 405 nm | 350 nm |
|---|---|---|---|---|---|
| 1 | 0.200 | 0.184 | 2.30 | 11.47 | 18.0 |
| 2 | 0.400 | 0.418 | 1.801 | 8.01 | 12.17 |
| 3 | 0.400 | 0.293 | 2.396 | 13.90 | 20.70 |
| 4 | 0.200 | 0.151 | 0.698 | 5.52 | 8.37 |
| 5 | 0.300 | 0.240 | 0.593 | 3.99 | 6.43 |
| 6 | 0.250 | 0.174 | 0.549 | 3.98 | 6.32 |
| 8 | 0.300 | 0.07 | 0.17 | 3.7 | 8.07 |

The foregoing examples illustrate various aspects of the invention and are not intended to provide an exhaustive description of the many different possible embodiments of the invention. Thus, those of ordinary skill in the art will realize readily that many changes and modifications can be made thereto without departing from the spirit or scope of the appended claims and their equivalents.

What is claimed is:

1. A population of nanocrystals, wherein each nanocrystal in the population comprises:
   a semiconductor core; and
   a semiconductor shell disposed on the semiconductor core, wherein an extinction coefficient of the population measured at an excitation wavelength of 405 nm is greater than 3,000,000 cm$^{-1}$M$^{-1}$, wherein the population has a maximum fluorescence emission wavelength in the visible portion of the electromagnetic spectrum below the red spectral region.

2. The population of nanocrystals of claim 1, wherein each nanocrystal in the population has a nanocrystal volume to core volume ratio ($V_{core+shell}/V_{core}$) of 10:1 or greater.

3. The population of claim 2, wherein greater than about 75% of the population of nanocrystals have average diameters of less than about 15 nm.

4. The population of claim 2, wherein the average core volume is about 100 nm$^3$ or less.

5. The population of claim 4, wherein the average core volume is about 50 nm$^3$ or less.

6. The population of claim 4, wherein the average nanocrystal volume is about 150 nm$^3$ or greater.

7. The population of claim 4, wherein the average nanocrystal volume is about 150 nm$^3$ to about 350 nm$^3$.

8. The population of claim 2, wherein at least a portion of the shell comprises about 3 monolayers to about 16 monolayers of semiconductor material.

9. The population of claim 2, wherein the extinction coefficient is about 30,000,000 cm$^{-1}$M$^{-1}$ or less.

10. The population of claim 2, wherein the population when irradiated emits light in a spectral range of no greater than about 40 nm full width at half maximum (FWHM).

11. The population of claim 2, wherein the population exhibits a QY of about 40% or greater.

12. The population of claim 2, wherein each nanocrystal comprises an external shell and an intermediate semiconductor shell, wherein the intermediate shell is disposed on the semiconductor core, wherein the intermediate and external shells are different.

13. The population of claim 2, wherein the semiconductor core and/or semiconductor shell comprises a Group II-VI, Group or Group II-VI-VI semiconductor material.

14. The population of claim 2, wherein the semiconductor shell comprises a semiconductor material selected from Cd, S, Se, Zn and combinations thereof.

15. The population of claim 2, wherein the semiconductor shell comprises a semiconductor material selected from ZnS, CdS, CdZnS, CdSeZn, ZnSeS, CdSeZnS and combinations thereof.

16. A method for producing the population of nanocrystals of claim 2, comprising:
  providing a reaction mixture including a plurality of semiconductor nanocrystal cores and at least one solvent;
  adding to the reaction mixture a first semiconductor shell precursor and a second semiconductor shell precursor; wherein the first and second semiconductor shell precursors are different; and
  heating the reaction mixture during addition of the first and second shell precursors for a period of time sufficient to induce formation of a first semiconductor shell on each of the plurality of nanocrystal cores, wherein the thickness of the shell is such that the nanocrystal volume to core volume ratio ($V_{core+shell}/V_{core}$) is 10:1 or greater, thereby producing a population of nanocrystals.

17. The population of nanocrystals of claim 1, wherein the nanocrystal volume to core volume ratio ($V_{core+shell}/V_{core}$) of each nanocrystal is greater than about 5:1.

18. The population of claim 1, wherein the maximum fluorescence emission wavelength is in the orange spectral region.

19. The population of claim 1, wherein the maximum fluorescence emission wavelength is in the yellow spectral region.

20. The population of claim 1, wherein the maximum fluorescence emission wavelength is in the green spectral region.

* * * * *